(12) United States Patent
Bakkers et al.

(10) Patent No.: US 7,825,032 B2
(45) Date of Patent: Nov. 2, 2010

(54) FABRICATING A SET OF SEMICONDUCTING NANOWIRES, AND ELECTRIC DEVICE COMPRISING A SET OF NANOWIRES

(75) Inventors: Erik Petrus Antonius Maria Bakkers, Eindhoven (NL); Louis Felix Feiner, Eindhoven (NL); Abraham Rudolf Balkenende, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 1088 days.

(21) Appl. No.: 10/584,037

(22) PCT Filed: Dec. 3, 2004

(86) PCT No.: PCT/IB2004/052651

§ 371 (c)(1),
(2), (4) Date: Jun. 21, 2006

(87) PCT Pub. No.: WO2005/064639

PCT Pub. Date: Jul. 14, 2005

(65) Prior Publication Data

US 2008/0224115 A1   Sep. 18, 2008

(30) Foreign Application Priority Data

Dec. 22, 2003  (EP)  ................................. 03104900

(51) Int. Cl.
*H01L 21/302*  (2006.01)

(52) U.S. Cl. ................. 438/707; 977/721; 257/E21.214

(58) Field of Classification Search ................. 438/707, 438/99, 706; 977/818, 963, 845, 887, 721; 257/E21.214
See application file for complete search history.

(56) References Cited

U.S. PATENT DOCUMENTS 4,518,456 A    5/1985  Bjorkholm
2002/0130311 A1    9/2002  Lieber et al.

OTHER PUBLICATIONS

Journal of Physical Chemistry B 2001, 105, 6838-6845 "Characterization of Ultrasmall CdS Nanoparticles Prepared by the Size-Selective Photoetching Technique" Tsukasa Torimoto, Hironori Kontani, Yoshihiro Shibutani, Susumu Kuwabata, Takao Sakata, Hirotaro Mori, and Hiroshi Yoneyama.*
"Different behavior of photoluminescence anisotropy in porous silicon layers made by polarized-light-assisted electrochemical etching" Hideki Koyama, Applied Physics Letters vol. 80, No. 6, Feb. 11, 2002. pp. 965-967.*
"Fabrication of Metal Nanowires Using Microcontact Printing" Matthis Geissler et al. 2003 American Chemical Society Langmuir 2003, 19, 6301-6311.*

* cited by examiner

*Primary Examiner*—Jack Chen

(57) ABSTRACT

The method of fabricating semiconducting nanowires having a desired wire diameter includes providing pre-fabricated semiconducting nanowires, at least one pre-fabricated nanowire having a wire diameter larger than the desired wire diameter (d); and reducing the wire diameter of the at least one pre-fabricated nanowire by etching. The etching is induced by light which is absorbed by the at least one pre-fabricated nanowire. The spectrum of the light is chosen such that the absorption of the at least one pre-fabricated nanowire is significantly reduced when the at least one pre-fabricated nanowire reaches the desired wire diameter.

18 Claims, 13 Drawing Sheets

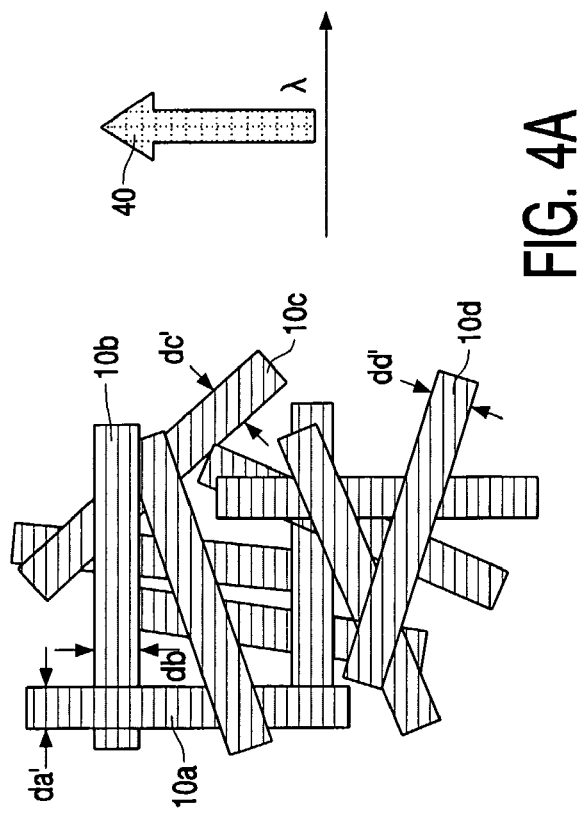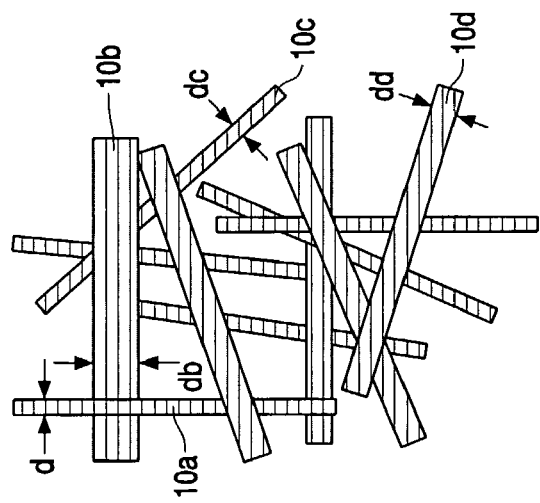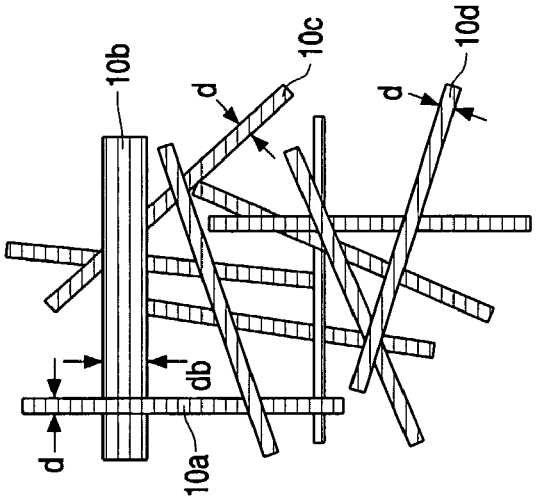
FIG. 4A
FIG. 4B
FIG. 4C

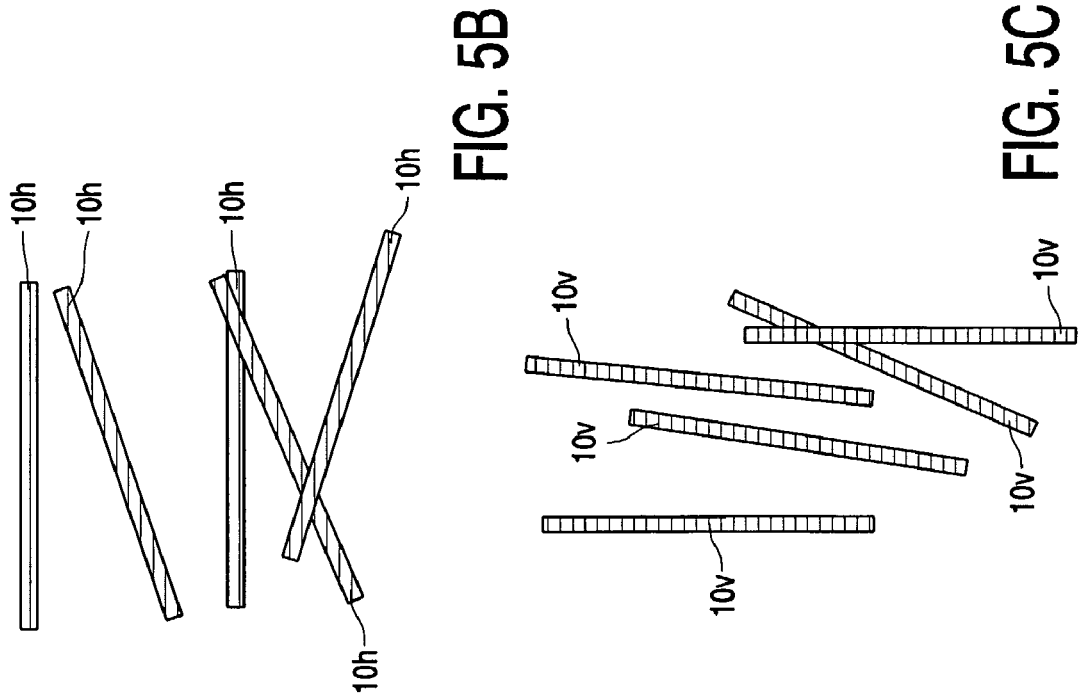
FIG. 5B
FIG. 5C
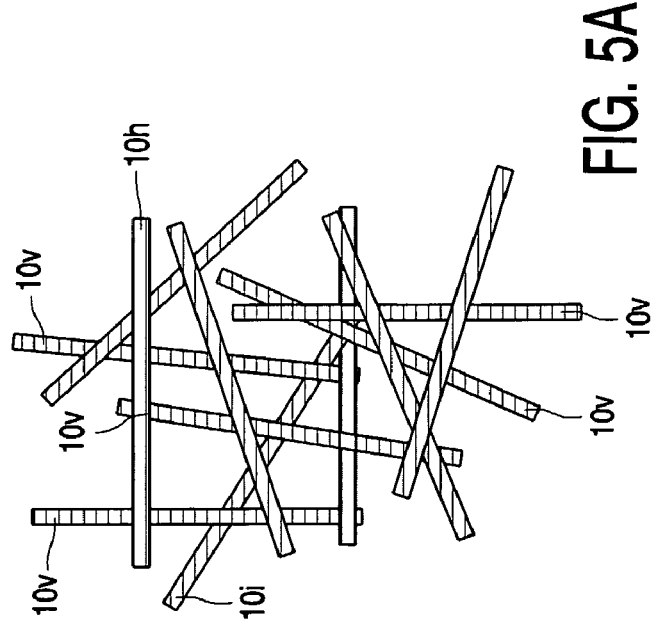
FIG. 5A

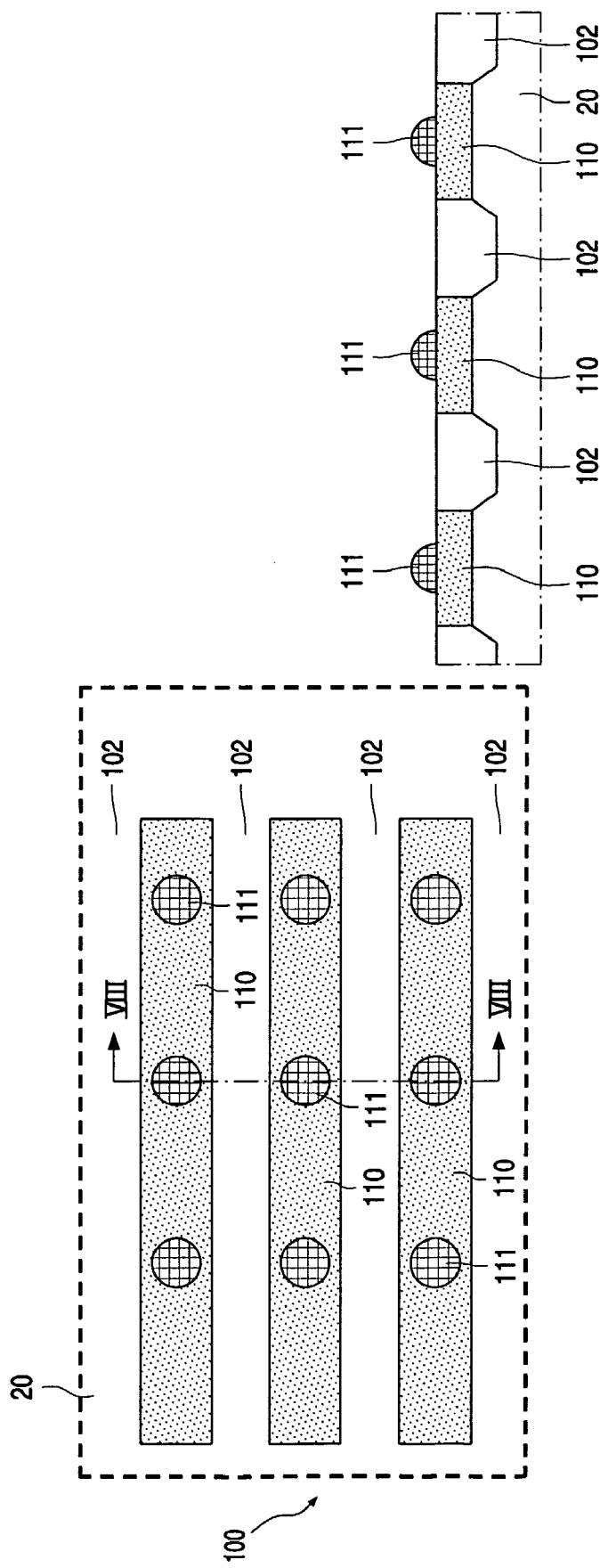

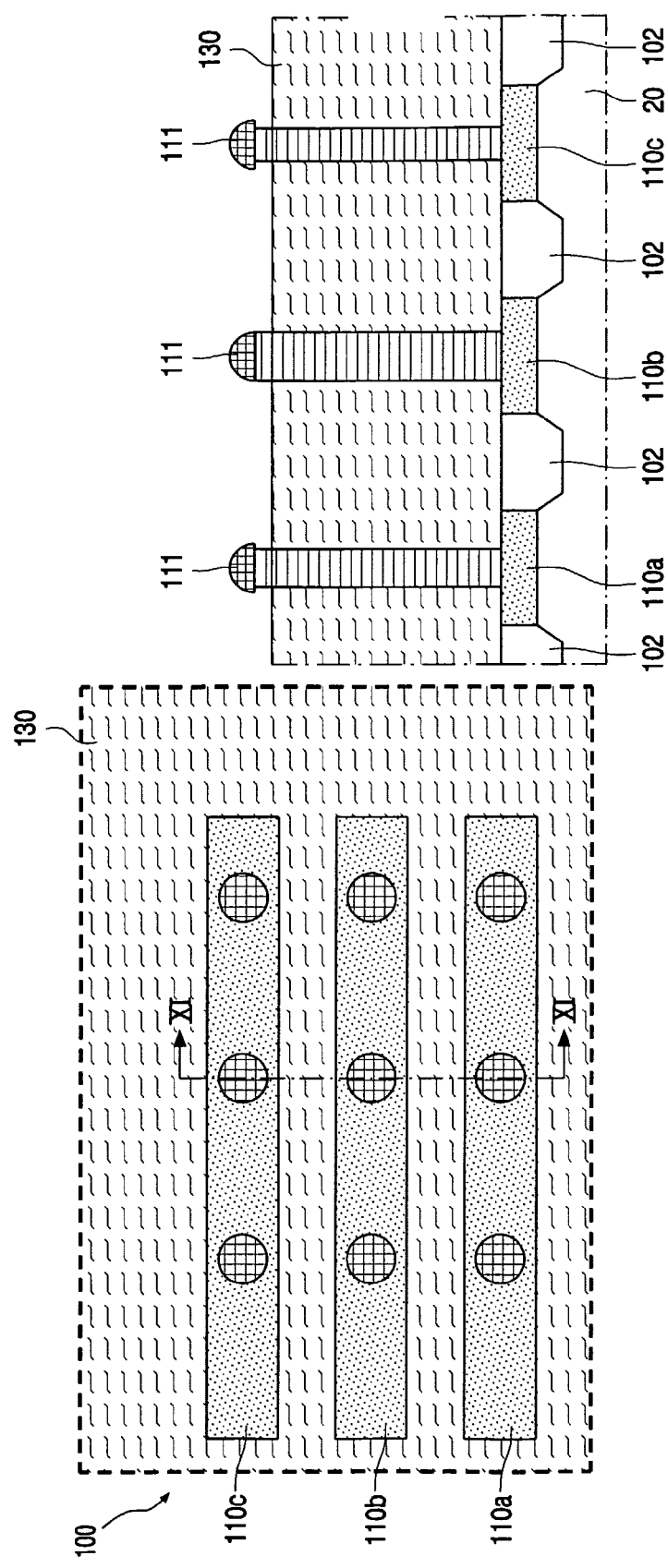

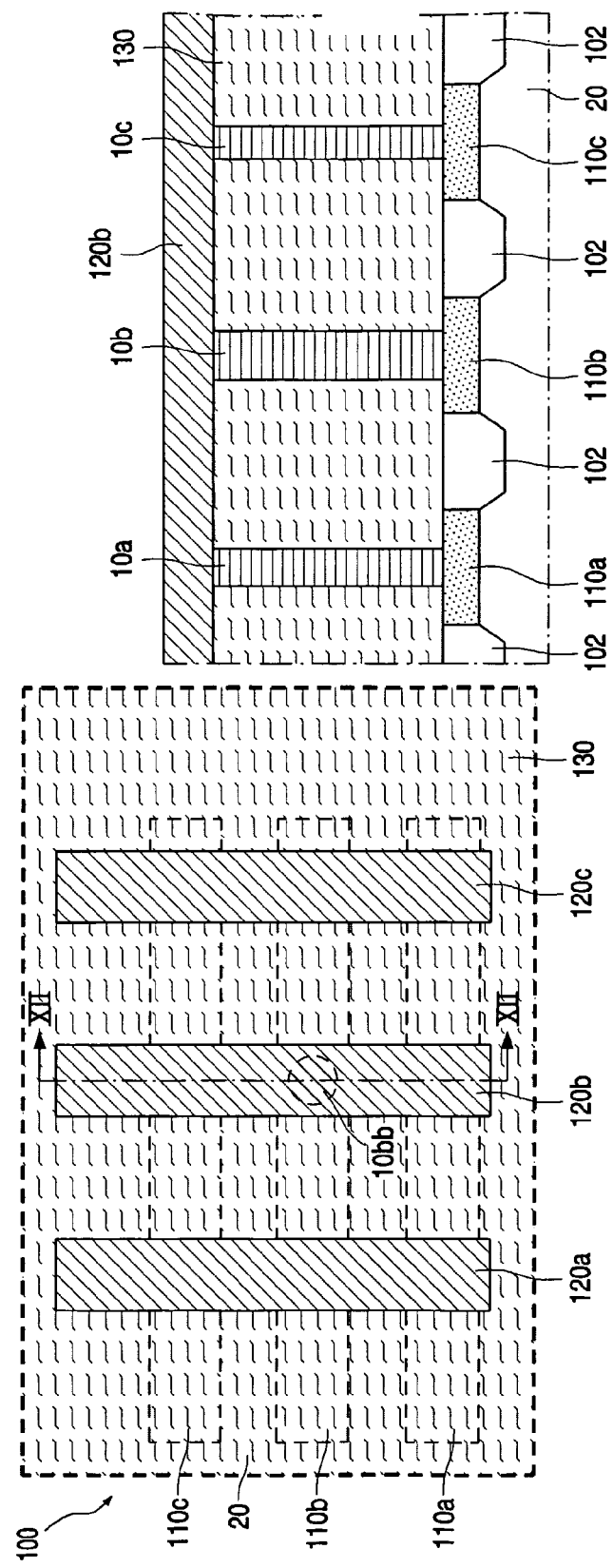

FABRICATING A SET OF SEMICONDUCTING NANOWIRES, AND ELECTRIC DEVICE COMPRISING A SET OF NANOWIRES

The invention relates to a method of and an apparatus for fabricating a set of semiconducting nanowires having a desired wire diameter.

The invention further relates to an electric device comprising a set of nanowires.

US-A1-2002/0,130,311 discloses an embodiment of a method of fabricating a set of semiconducting nanowires having a desired wire diameter. Nanowires are quasi one-dimensional conductors or semiconductors. They extend along a longitudinal axis and have a wire length along this longitudinal axis from hundred nanometers or below to several micrometers or even longer. Perpendicular to the longitudinal axis the nanowires have a wire diameter, which leads to quantum confinement effects described below and which is smaller than typically a few hundred nanometers. The wire diameter may be below 100 nm and may range, e.g., between 2 and 20 or 50 nm. Due to the relatively small dimensions perpendicular to the longitudinal axis charge carriers such as electrons and holes are confined perpendicular to the longitudinal axis, i.e. in a radial direction. As a consequence the charge carriers have discrete quantum mechanical energy levels, which are determined by the wire diameter. In contrast to this, due to the relatively large dimension along the longitudinal axis, the charge carriers are not confined in discrete quantum mechanical energy levels as function of the wire length.

In the known method GaP nanowires are grown by a laser catalytic growth (LCG) process, i.e. the Ga and P reactants are generated by laser ablation of a solid GaP target. The GaP target comprises a relatively small amount of gold, which serves as a catalyst for the nanowire growth. The diameter of the nanowires thus obtained is relatively poorly defined. Alternatively, the target may be free of the catalyst and the reactants may be directed into a nanowire structure by gold nanocluster catalysis. To this end, catalyst nanoclusters, also called nanodots, supported by a $SiO_2$ substrate may be used. The reactants and the gold nanodots produce nanowires via a vapor-liquid-solid (VLS) growth mechanism. For growing wires having the desired diameter, nanodots having a size, which is similar to the desired wire diameter, are used. The nanowires grown in this way have on average a wire diameter, which is determined by the average size of the nanodots.

It is a disadvantage of the known method that the wire diameter is not well controlled, i.e. often at least one of the nanowires does not have the desired wire diameter. In the known method nanodots having a size, which is similar to the desired wire, diameter and which are supported by a substrate are required. When erroneously one or more nanodots having a wrong diameter are used, one or more nanowires having a wire diameter different from the desired wire diameter are obtained. Moreover, it may happen that during the VLS growth, which requires relatively high temperatures, one or more of the nanodots detach from the substrate and cluster with one or more other nanodots. From the resulting cluster of nanodots a nanowire is grown whose wire diameter is determined by the size of the cluster of the nanodots rather than by the size of a single nanodots, yielding a nanowire with a wire diameter, which is larger than the desired wire diameter. In order to reduce and ideally prevent this unwanted clustering the density of the catalyst nanoparticles and thus of the nanowires has to be relatively low.

It is an object of the invention to provide a method of fabricating a set of semiconducting nanowires in which the wire diameter is relatively well controlled.

According to the invention this object is realized in that the method comprises the steps of providing a set of pre-fabricated semiconducting nanowires, at least one pre-fabricated semiconducting nanowire having a wire diameter larger than the desired wire diameter, and reducing the wire diameter of the at least one pre-fabricated nanowire by etching, the etching being induced by electromagnetic radiation which is absorbed by the at least one pre-fabricated nanowire, a minimum wavelength of the electromagnetic radiation being chosen such that the absorption of the at least one pre-fabricated nanowire being significantly reduced when the at least one pre-fabricated nanowire reaches the desired wire diameter.

In order to reduce the wire diameter of the at least one pre-fabricated semiconducting nanowire having a wire diameter larger than the desired wire diameter, the set of pre-fabricated semiconducting nanowires is subjected to an etch treatment induced by electromagnetic radiation. The etch treatment induced by electromagnetic radiation, which is known, e.g., from U.S. Pat. No. 4,518,456, is a method in which a semiconducting object to be etched is placed in an, e.g. aqueous, solution of, e.g., $H_3PO_4$ or HCl. While the object is in contact with the solution, the parts of the object to be etched are illuminated by electromagnetic radiation. The electromagnetic radiation may be visible or invisible to the human eye and is referred to in the remainder of this application simply as "light". The light is at least partly absorbed by the object to be etched, thereby generating electrons and holes. These light generated charge carriers, i.e. the electrons and/or the holes, then diffuse and induce chemical reactions at the interface between the object and the solution. In the course of these chemical reactions, which are in the art also referred to as photo etching, atoms of the nanowire may be ionized and dissolved in the solution. The ionization of these atoms may be induced by the light generated charge carriers such as e.g. the holes. The process of dissolving the ions thus generated may involve the combination of these ions with ions in the solution. These latter ions may be induced by the light generated charge carriers such as e.g. the electrons. For InP in a Fluorine comprising solution six holes may form $In^{3+}$ and $P^{3+}$ ions out of InP. These positive ions may combine with negative Fluorine ions $F^-$ that may be formed by a reaction $F_2+2$ electrons resulting in $2F^-$. Similar processes known in the art may be used for other nanowire compositions.

In this application the term "semiconducting" describes the class of materials in which electron hole pairs may be generated by light to induce etching, e.g. in the way described above. If not stated differently, in the remainder of the application the term "nanowire" implies a semiconducting nanowire.

As described above, the etching requires the absorption of light by the pre-fabricated nanowire. Due to the quantum mechanical confinement the quantum mechanical energy levels available to the electrons and holes generated by the light depend on the wire diameter. As the wire diameter is reduced, the spacing between the levels, i.e. the spacing between the conduction band and the valence band, also referred to as the bandgap, is increased and, correspondingly, a larger energy is required to generate an electron hole pair.

When light having a given wavelength λ is used, there is a certain wire diameter at which the energy of a photon is no longer sufficient to generate an electron-hole pair. As a consequence the etching efficiency is largely reduced. The etching process effectively stops, i.e. the etch treatment is self-terminating. By choosing the spectrum of the light, and in particular the shortest wavelength, in the remainder referred to as the minimum wavelength of the spectrum, appropriately, it may be achieved that the etch treatment is self-terminating when the at least one pre-fabricated nanowire has the desired wire diameter. Due to this self-termination the wire diameter is relatively well controlled in the obtained set of semiconducting nanowires. The method has the additional advantage that the wire diameter is not dependent on the size of the nanodots used in the known method to control the wire diameter. Therefore, after etching the nanowires according to the invention, the size of the nanodots is not critical and incidental clustering of the nanodots does not result in nanowires having a wire diameter larger than the desired wire diameter.

Each desired wire diameter corresponds to a certain wavelength the value of which depends on the chemical composition of the nanowires. In general it holds that for a smaller wire diameter a shorter wavelength of the light is required. Instead of light having a single wavelength, light comprising several spectral components each having different wavelengths may be used, provided that the shortest wavelength corresponds to the desired wire diameter. In other words, a spectrum of the light is chosen such that the absorption of the at least one pre-fabricated nanowire is significantly reduced when the at least one pre-fabricated nanowire reaches the desired wire diameter.

For nanowires the quantum mechanical energy levels available to the electrons and holes generated by the light do not depend on the wire length, as discussed above. Therefore, the method according to the invention works for all nanowires independent of their wire length.

From the article "Etching of colloidal InP nanocrystals with fluorides: photochemical nature of the process resulting in high photoluminescence efficiency" by D. Talapin et al., Journal of Physical Chemistry B, 2002, volume 106, page 12659-12663, it is known that nanodots having a size of 5.2 nm or less can be etched. According to this article the etching is induced by light that is absorbed by the nanodots. The spectrum of the light is chosen such that the absorption of the nanodots is significantly reduced when the nanodots reach the desired size.

For nanodots the quantum mechanical energy levels available to the electrons and holes generated by the light depend on the size of the nanodots, i.e. on the dimensions in all three directions. In contrast, the method according to the invention is independent from one of the three dimensions, i.e. from the wire length. Therefore, the method according to the article by Talapin does not work for all nanowires independent of their wire length.

The provided pre-fabricated nanowires may be obtained by any known method for manufacturing nanowires such as the LCG or the VLS method. Alternatively, the nanowires may be obtained e.g. by etching them from a single crystal.

The pre-fabricated nanowires may be attached to a substrate, they may be dispersed in a liquid solution or they may be laying loosely on a substrate.

The set of nanowires may comprise one or more nanowires.

The desired wire diameter may be one diameter or, when the set of nanowires comprises more than one nanowire, it may be a number of wire diameters for the respective nanowires.

The set of nanowires may comprise a selection of the nanowires comprised on a substrate or in a solution.

The nanowires may be of a homogeneous composition, i.e. they may have the same chemical composition as function of the wire diameter and the wire length. Alternatively, some or all nanowires may be of a heterogeneous composition, i.e. they may have a chemical composition which is a function of the wire diameter and/or the wire length. The chemical composition may be changed due to doping of the semiconducting nanowire, which depends on the wire diameter and/or the wire length.

In this application the term "nanowire" describes both nanowires with a solid core and nanowires with a hollow core. The latter are also referred to in the art as nanotubes. Also in the latter type of nanowires charge carriers such as electrons and holes are confined perpendicular to the longitudinal axis, i.e. in a radial direction, due to the relatively small dimensions perpendicular to the longitudinal axis. As a consequence the charge carriers have discrete quantum mechanical energy levels, which are determined mainly by the thickness of the core defining this type of nanowire. Due to the relatively large dimension along the longitudinal axis, the charge carriers are not confined in discrete quantum mechanical energy levels as function of the wire length, analogous to the nanowires having a solid core. When the nanowire has a hollow core, the wire diameter refers to the thickness of the core. The thickness of the core is the difference between the outer wire diameter and the inner wire diameter, i.e. the diameter of the hollow part.

In an embodiment a radiation source is used which emits the electromagnetic radiation inducing the etching and in addition to this also electromagnetic radiation having a wavelength shorter than the minimum wavelength. The electromagnetic radiation emitted by the radiation source is spectrally filtered for substantially reducing electromagnetic radiation having a wavelength shorter than the minimum wavelength. This latter electromagnetic radiation having a wavelength shorter than the minimum wavelength is able to induce etching of the pre-fabricated semiconducting nanowires having the desired wire diameter, i.e. it has a wavelength which is shorter than the wavelength at which the etching process terminates at the desired wire diameter. Prior to directing the electromagnetic radiation onto the pre-fabricated nanowires, the electromagnetic radiation emitted by the radiation source is spectrally filtered for substantially reducing electromagnetic radiation having a wavelength shorter than the minimum wavelength. In this way etching of pre-fabricated semiconducting nanowires having the desired wire diameter is substantially reduced and preferably effectively prevented. In this application the term "light source" is used as a synonym for the term "radiation source". The term "light source" is not limited to radiation sources which emit visible electromagnetic radiation but may include radiation sources which emit electromagnetic radiation invisible to the human eye.

In an embodiment the pre-fabricated semiconducting nanowires have a diameter larger than or equal to the desired wire diameter prior to the step of reducing the wire diameter. During the step of reducing the wire diameter the pre-fabricated nanowires having a wire diameter larger than the desired wire diameter are etched until they have the desired wire diameter. In this way a set of nanowires is obtained which substantially has the same desired wire diameter, which is determined by the shortest wavelength comprised in the spectrum. As the band gap of the nanowires is directly related to the termination of the light induced etching, substantially all nanowires of the set have the same band gap, which is determined by the shortest wavelength comprised in the spectrum.

The light inducing the etch treatment may be linearly polarized along an axis. In general, the absorption of light by a semiconducting nanowire is polarization selective. Light polarized parallel to the longitudinal axis of a nanowire is absorbed much more efficiently by the nanowire than light polarized perpendicular to this axis. This difference is particularly large when the medium surrounding the semiconducting nanowire has a dielectric constant, which is different from that of the semiconducting nanowire. By using linearly polarized light the etching efficiency depends on the orientation of the nanowires: nanowires oriented parallel to the axis are etched relatively efficiently whereas nanowires oriented perpendicular to the axis are etched relatively inefficiently. Intermediate nanowires having an orientation of their longitudinal axis, which is neither parallel nor perpendicular to the axis of the polarization, are etched with an intermediate etching efficiency which is a function of the angle between the longitudinal axis and the axis of the polarization. In this way a set of nanowires having an orientation dependent wire diameter may be obtained.

The light inducing the etch treatment may comprise a first component linearly polarized along a first axis and a second component linearly polarized along a second axis forming an angle larger than zero with the first axis. In this way it is possible to etch the nanowires oriented parallel to the first axis in a different way than the nanowires oriented parallel to the second axis. The first axis may be perpendicular to the second axis. To this end the spectral properties and/or the intensity of the two components may be adjusted. The first component and the second component may be provided simultaneously or sequentially, i.e. one after the other. Alternatively, they may be provided partly simultaneously, i.e. for a certain time period both components are provide together and another time period one of the two components is proved but not the other.

When the first component has a first spectrum with a first minimum wavelength and the second component has a second spectrum with a second minimum wavelength different from the first minimum wavelength, nanowires oriented parallel to the first axis are etched to a wire diameter determined by the first minimum wavelength whereas nanowires oriented parallel to the second axis are etched to a wire diameter determined by the second minimum wavelength. It is thus possible to obtain a chemically homogeneous set of nanowires, which have different wire diameters, depending on their orientation. In other words, a set of nanowires with a homogeneous chemical composition is obtained which has an anisotropic band gap.

Another way to obtain an anisotropic distribution of band gaps in the set of nanowires is based on the dependence of the etch rate on the absorption and hence on the intensity of the light. In one embodiment the first component has a first intensity and the second component has a second intensity different from the first intensity. As a result an, e.g. randomly oriented, set of nanowires is etched orientation dependent. The nanowires being mainly parallel to the first axis are etched more efficiently than the nanowires being mainly parallel to the second axis. In one embodiment the second intensity is substantially zero and the nanowires parallel to the second axis are not etched at all. As a result, a set of nanowires with the desired wire diameter may be obtained, all of the nanowires of the set having a longitudinal direction parallel to the second axis.

According to another aspect of the invention the desired wire diameter may comprise zero, i.e. at least one pre-fabricated nanowire is effectively removed from the set of pre-fabricated nanowires by etching induced by light. The inventors have gained the insight that nanowires having a wire diameter smaller than a certain threshold value are no longer stable, i.e. they fall apart and are effectively etched away. The threshold value depends in general on the chemical composition of the nanowire and may be well below 3 nm such as e.g. approximately 1 nm.

The instability of the nanowires having a wire diameter below or equal to the threshold value may be used to remove a nanowire from the set of pre-fabricated nanowires. To this end light comprising a wavelength, which is absorbed by a nanowire having a wire, diameter below or equal to the threshold value is used. This light induces etching of the nanowire down to a wire diameter at which the nanowire falls apart and thus disappears.

When the light inducing etching of nanowires having a desired wire diameter of zero is linearly polarized, nanowires having their longitudinal axis parallel to the polarization of the light may be removed, whereas nanowires having their longitudinal axis perpendicular to the polarization direction of the light are etched much less efficiently. In this way, substantially all nanowires parallel to the polarization direction may be removed. When light is applied even longer, substantially all nanowires, which are not substantially perpendicular to the polarization direction, are removed and a set of nanowires oriented along an axis perpendicular to the polarization direction is obtained. As the remaining nanowires have not been etched efficiently, they may have a substantially unchanged distribution of wire diameters.

The prefabricated nanowires may be distributed on a surface or in a volume and the light inducing etching of nanowires having a desired wire diameter of zero may be supplied to a part of the surface or the volume. As a result the nanowires may be removed from the illuminated part of the surface or the volume but not from the remainder of the surface of the volume. The part to be illuminated may be illuminated by focusing the light on that part. Alternatively or in addition the light may be partly blocked by a mask such as, e.g. a lithography mask.

According to another aspect of the invention the pre-fabricated semiconducting nanowires may be supported by a substrate. The pre-fabricated semiconducting nanowires may be lying on the surface, they may be attached to the surface and/or they may be chemically bound to the surface. As described above, the light induced etching treatment is self-terminating due to the quantum confinement of the charge carriers in the nanowire. The inventors have gained the insight that this quantum confinement is not significantly disturbed when the nanowire is supported by a substrate. This is surprising in so far as the vicinity of the substrate in general changes the quantum mechanical energy levels available to the charge carriers. However, the inventors observed that this change of the quantum mechanical energy levels is relatively small and the etching is self terminated at substantially the same wire diameter. This effect occurs even when the substrate is an electrical conductor and the pre-fabricated semiconducting nanowires are electrically conductively connected to the substrate. Such a substrate with nanowires attached to it is a very good starting point for the manufacturing of an electric device comprising such a nanowire.

The substrate may have a surface constituted by a part supporting the pre-fabricated semiconducting nanowires and another part being free from the part, at least the other part being etch resistant. The term etch resistant implies that the light induced etching does not or substantially not modify the surface. In this way the surface of the substrate is not etched during the etching of the nanowires. It substantially remains in its initial shape. This is in particular advantageous when the nanowires supported by the substrate are attached to the substrate because otherwise the nanowires may get detached during the etch treatment which may complicate further use of the nanowires in, e.g., an electric device.

The substrate may be of a homogenous composition which is etch resistant. In another embodiment, the substrate comprises a first layer, which is not etch resistant, and a second layer, which is etch resistant, the second layer constituting the surface. The combination of the first layer and the second layer allows to obtain the desired etch resistant surface while other desired properties of the substrate, which may be not provided by the second layer alone, may be provided by the first layer. The first layer may be, e.g., mechanically rigid whereas the second layer alone, i.e. without the first layer is not mechanically rigid. The first layer may be electrically conducting whereas the second layer alone is insulating. It is often advantageous if the second layer is connected to the first layer by a chemical bond which is etch resistant, i.e. substantially not broken by the etch treatment. This assures that the first layer is well protected by the second layer during the etch treatment, resulting in an intact substrate after the etching.

It is advantageous if the second layer is composed of one or more materials selected from alkyltriethoxysiloxane and alkyltrimethoxysiloxane. These materials may form a layer which effectively protects the first layer which may be composed of one or more elements selected from silicon, silicon oxide, aluminum oxide, metals such as e.g. Platinum or a polymer. The above mentioned materials for the second layer have the advantage that relatively thin layers of, e.g. one, monolayer already result in an effective protection of the first layer. This is in particular advantageous because the nanowire may be partly surrounded by the second layer, the surrounded part being protected against etching as well. This results in a nanowire which is not etched or less effectively etched at its end supported by the substrate. By using a relatively thin second layer, the part of the nanowire which is not etched or less effectively etched, is kept small.

When the step of providing the pre-fabricated semiconducting nanowires comprises the sub-steps of providing the substrate, the substrate being not etch resistant, and growing semiconducting nanowires on a surface of the substrate, the grown semiconducting nanowires being the pre-fabricated semiconducting nanowires, it is advantageous if the surface of the substrate which is exposed after the step of providing the pre-fabricated semiconducting nanowires, is covered by an etch resistant layer prior to the step of reducing the wire diameter of the at least one pre-fabricated nanowire by etching. In other words, the etch resistant layer is provided after growing the nanowires. Growing the nanowires by, e.g., VLS growth requires relatively high temperatures. By providing the etch resistant layer after the growths of the nanowires, it is assured that the etch resistant layer is not subjected to these relatively high temperatures. It is thus possible to use an etch resistant layer composed of a material which cannot withstand these temperatures.

In a number of embodiments, the pre-fabricated semiconducting nanowires are distributed over a surface area of the substrate. It is then advantageous to illuminate a part of the surface area by a first light intensity while another part of the surface free from the part of the surface is irradiated by a second light intensity smaller than the first light intensity. In this way relative effective etching of pre-fabricated semiconducting nanowires in the part of the surface is induced while pre-fabricated semiconducting nanowires in the other part of the surface are etched substantially less efficient because the etching efficiency scales with the light intensity. In this way a substrate may be obtained which has nanowires of the different wire diameter in the part and the other part. To this end the illumination may be stopped when the wire diameter of the nanowires in the part of the surface is not changed anymore due to self-termination of the etching process. When integrating both parts in a light-emitting device, two different colors corresponding to the two different wire diameters may be obtained. In one embodiment the second light intensity is substantially zero, i.e. the nanowires on the other part of the surface are substantially not etched.

In another embodiment the pre-fabricated semiconducting nanowires are distributed over a surface area of the substrate, a first part of the surface area being irradiated by light having a first minimum wavelength, a second part of the surface free from the part of the surface being irradiated by light having a second minimum wavelength different from the first wavelength. Also in this case a substrate may be obtained which has nanowires of the different wire diameter in the part and the other part. When the nanowires are etched until the etching is self-terminated, the wire diameters are determined by the first minimum wavelength and the second minimum wavelength, respectively. This has the advantage that the control of the wire diameter is relatively reliable as compared to the embodiment described above.

An electric device according to the invention may comprise a set of semiconducting nanowires, the set comprising a first subset of nanowires each having a first wire diameter and a second subset of nanowires each having a second wire diameter different from the first wire diameter, the nanowires of the first subset being attached to a first part of a substrate, the nanowires of the first subset being attached to a second part of the substrate free from the first part. Such an electric device may be e.g. a light emitting device in which light of a different wavelength may be emitted by the nanowires of the first and second subset, respectively. The electric device may be an integrated circuit in which the nanowires serve as semiconducting elements whose electrical behavior depends on the bandgap and hence on the wire diameter. Examples are transistors such as metal oxide semiconductor field effect transistors (MOSFET) in which the nanowire constitutes the semiconducting substrate and bipolar transistors. The threshold voltage of the MOSFET depends on the band gap of the nanowire. Thus transistors with different threshold voltages may be obtained in the same electric device. Alternatively or in addition, the semiconducting element may comprise a diode.

The nanowires of the first subset may be electrically connected to a conductor, the nanowires of the second subset may be electrically connected to a further conductor element which is electrically insulated from the conductor. In this way the nanowires of the first subset may be addressed independently from those of the second subset by means of electrical current.

The nanowires may comprise a p-doped part and an n-doped part forming a p-n junction. This p-n junction may constitute a diode with electrical characteristics depending on the wire diameter. The electrical device may comprise electrical diodes of different characteristics. The diode may serve as a light emitting diode. At least one of the n-doped part and the p-doped part may be a direct semiconductor.

The n-doped part may be electrically connected to a first conductor having a first distance to the p-n junction, the p-doped part may be electrically connected to a second conductor having a second distance to the p-n junction smaller than the first distance. In general the conductance of the p-doped part is lower than that of the n-doped part. Therefore, the electrical current is relatively high when the p-doped part is shorter than the n-doped part.

The n-doped part may have a wire diameter which is larger than the wire diameter of the p-doped part. The mobility of the majority charge carriers in the p-doped part, i.e. of the holes, is lower than that of the majority charge carriers in the n-doped part, i.e. of the electrons. Therefore, the recombination takes place mainly in the p-doped part. The wavelength of the light emitted when an electron and a hole recombine is determined mainly by the wire diameter of the part in which the recombination takes place, i.e. by the wire diameter of the p-doped part. The wire diameter of the p-doped part and thus the wavelength may be controlled by using the method according to the invention. When the wire diameter of the n-doped part is larger than that of the p-doped part, the resistance of the n-doped part is reduced leading to a higher current flow whereas the wavelength of the light emitted is mainly determined by the wire diameter of the p-doped part. In this way a light emitting diode emitting a relatively short wavelength and having a relatively high brightness may be obtained.

These and other aspects of the method of fabricating a set of semiconducting nanowires according to the invention will be further elucidated and described with reference to the drawings, in which:

FIGS. 4A, 4B and 4C are schematic top views of a set of prefabricated nanowires prior to the etch treatment, after an etch treatment induced by linearly polarized light for a first time period and for a second time period longer than the first time period, respectively;

FIGS. 5A, 5B and 5C are schematic top views of a set of prefabricated nanowires prior to the etch treatment, after an etch treatment induced by linearly polarized light along a first axis and along a second axis perpendicular to the first axis, respectively;

FIGS. 8A and 8B are a schematic top view and a respective schematic cross sectional view along line VIII-VIII of FIG. 8A of an electric device comprising a set of prefabricated nanowires at a first stage of the manufacturing process;

FIGS. 11A and 11B are a schematic top view and a respective schematic cross sectional view along line XI-XI of FIG. 11A of an electric device comprising a set of prefabricated nanowires at a fourth stage of the manufacturing process;

FIGS. 12A and 12B are a schematic top view and a respective schematic cross sectional view along line XII-XII of FIG. 12A of an electric device comprising a set of prefabricated nanowires at a fifth stage of the manufacturing process.

The Figures are not drawn to scale. In general, identical components are denoted by the same reference numerals.

Figure 1A:
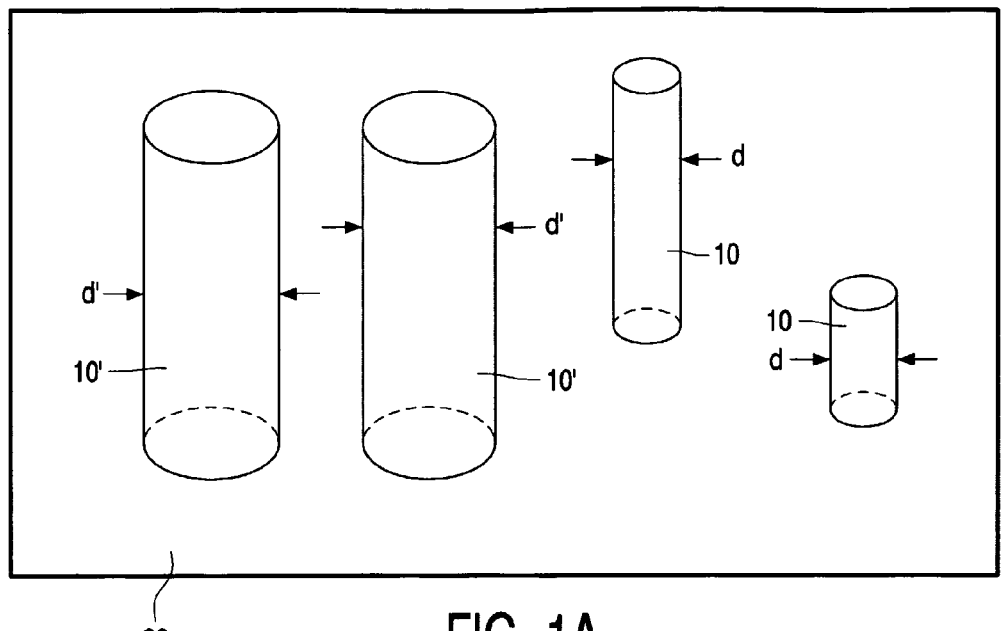
FIGS. 1A and 1B are perspective views of a substrate with attached to it prefabricated nanowires prior to the etch treatment and after the etch treatment, respectively.

In the method of fabricating a set of semiconducting nanowires having a desired wire diameter according to the invention, first a set of pre-fabricated semiconducting nanowires 10 is provided. The nanowires 10 may be obtained in the following way:

A substrate 20 such as, e.g., a wafer of silicon or of a III-V semiconductor such as e.g. GaAs which may have a native oxide, or an insulating plate of e.g. aluminum oxide or silicon oxide is provided with an equivalent of an, e.g. 4, Angstrom of a metal such as Au, Ag, Pt, Cu, Fe, Ni or Co and placed on an insulating substrate holder of e.g. aluminum oxide, silicon oxide, ceramic or graphite at the downstream end of an oven. The substrate temperature is measured 1 mm below the substrate by the use of a thermo couple. When the substrate with the metal film is heated to approximately 500 degree Celsius, nanoparticles are formed out of the metal film which nanoparticles may act as a catalyst for the growth of the nanowires 10. The thickness of the metal film may be between, e.g., 2 and 60 Angstrom. The thicker the metal film, the larger is the wire diameter of the nanoparticles. Heating a metal film composed of gold having a thickness of 5 Angstrom at 470 degrees Celsius, nanowires with a diameter of 40 nm are obtained.

A pulsed excimer laser operating at a wavelength of $\lambda=193$ nm, 100 mJ per pulse and at a repetition rate of 1-10 Hz is focused on a target, which is placed 3-4 cm outside an oven at the upstream end of a quartz tube of an oven. The target may be an InP target. Alternatively, the target may comprise one or more targets selected from e.g. Si, Ge, InAs, GaP and GaAs. In general, the material may be any group IV, III-V or II-VI semiconducting material.

The target material is vaporized and transported over the substrate 20. This results in the growth of nanowires 10 under the catalysis of the nanoparticles formed out of the metal film. InP nanowires are grown when the substrate temperature is in the range 450-500° C. The higher the temperature, the larger is the wire diameter of the nanowires grown. At a temperature above 500° C. InP nanotubes, i.e. a nanowire with a hollow core, may be formed. The pressure during growth is in the range 100-200 mbar and an argon flow between 100-300 sccm is applied. The length of the nanowires may be, e.g., 2-10 micron when 15000 laser pulses are applied. Shorter and longer nanowires may be obtained with less and more laser pulses, respectively. The resulting wire diameter is determined by the thickness of the metal film and by the substrate temperature during growth. Dopants may be added at a concentration of, e.g. 0.001-1.0 mol % to obtain n-type and/or p-type InP nanowires. The n-type dopants may comprise e.g. S, Se and Te, the p-type dopants may comprise e.g. Zn. The dopants may be added to the target illuminated by the excimer laser or they may be provided as a gas to the oven, independent from the illumination of the target. The resulting level of active dopants in the nanowire is $10^{17}$-$10^{20}$ atoms/cm$^3$. E.g. by shifting the laser beam to another target, e.g. selected from one of the targets described above, during the growth process, a junction may be built in the wire, i.e. a p-n junction and/or hetero-junction.

The pre-fabricated semiconducting nanowires 10 thus obtained are supported by the substrate 20, shown in FIG. 1A. At least one pre-fabricated semiconducting nanowire 10' has a wire diameter d' larger than the desired wire diameter d. The wire diameter d' may be due to clustering of two or more nanoparticles during the growth of the nanowires 10 and/or due to deposition of a too thick metal film and/or due to a too high temperature during the synthesis of the nanowires 10.

The substrate 20 may be an electrical conductor such as an, e.g. p-doped or n-doped, silicon wafer. The pre-fabricated semiconducting nanowires 10 may be electrically conductively connected to the substrate 20. To this end the metal film may be deposited on a substrate 20 which does not have a native oxide film. When the nanoparticles acting as catalyst and the nanowires 10 are formed in an oxygen-free atmosphere, the nanowires 10 may be electrically conductively connected to the substrate 20.

Subsequently, the wire diameter d' of the at least one pre-fabricated nanowire 10' is reduced by etching. To this end an etch solution is prepared by adding 0.1-20 vol % HF such as e.g. 2.5 vol. % and 20-200 g/l such as 62.5 g/l trioctylphosphideoxide (TOPO) to a sample of an alcohol such as e.g. 1-butanol, pentanol, propanol or ethanol. Instead or in addition to TOPO trioctylphosphide (TOP) may be used. The total quantity of TOP and TOPO may be between 20-200 g/l. A droplet of e.g. 20 µl of the etch solution 21 thus obtained is drop-casted onto the substrate 20 with the pre-fabricated nanowires 10. A glass or Teflon coated plate 22, shown in FIG. 2, may be placed on top of the droplet to avoid evaporation of the solution. The plate 22 may be supported by support structure, not shown, to obtain a well defined thickness of the etch droplet 21.

The nanowires 10 are etched by subjecting the nanowires 10 which are in contact with the etch solution to light. The etching of the nanowires 10 is induced by light absorbed by them. The spectrum of the light is chosen such that the absorption of the at least one pre-fabricated nanowire 10' is significantly reduced when the at least one pre-fabricated nanowire 10' reaches the desired wire diameter d. For a desired wire diameter d of 6, 10, 30, 44 and 60 nm of an InP nanowire the minimum wavelength is approximately 760, 820, 870, 890 and 905 mm, respectively. The emission of bulk InP is at $\lambda=920$ nm.

Figure 1B:
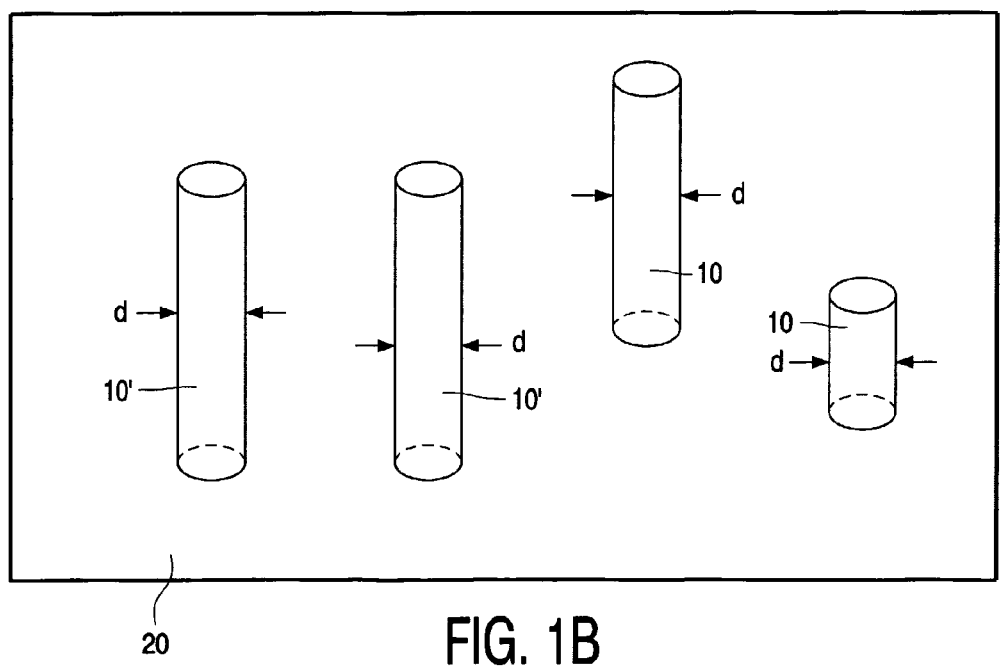

This self-termination of the light induced etching is due to the quantum confinement which limits the absorption of the light below a certain wire diameter as described above. The result after this etch treatment shown in FIG. 1B is that the pre-fabricated nanowire 10' has the desired wire diameter d.

In an embodiment substantially all the pre-fabricated nanowires 10' have a diameter d' larger than or equal to the desired wire diameter d prior to the step of reducing the wire diameter. To this end the metal film used for forming the catalyst nanoparticles may be relatively thick such that substantially all pre-fabricated nanowires have a wire diameter larger than the desired wire diameter. After performing the etching treatment substantially all nanowires have the desired wire diameter d. The terms "substantially all the pre-fabricated nanowires" and "substantially all the nanowires" imply that the pre-fabrication of the nanowires 10' is designed to produce nanowires having a diameter d' larger than the desired diameter d. Due to incidental unwanted formation of one or a few small nanoparticles out of the metal film one or a few of the nanowires may have a wire diameter d' which is accidentally smaller than the desired wire diameter d.

Figure 2:
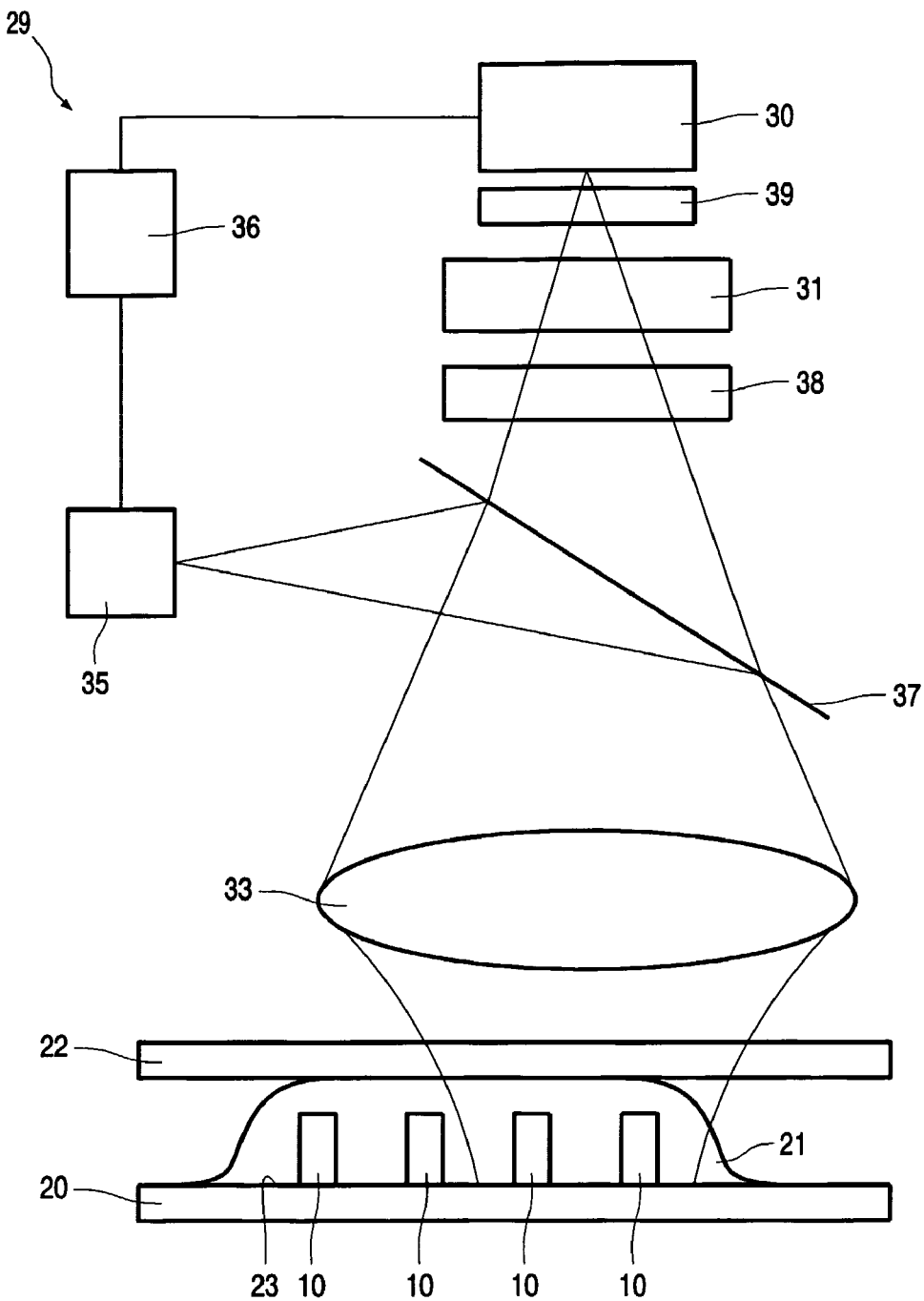
FIG. 2 is a is a schematic diagram of an apparatus used for executing the method according to the invention.

For the light induced etching an apparatus 29 shown schematically in FIG. 2 may be used. The apparatus comprises a light source 30, which may be, e.g., a HgXe lamp, for illuminating the pre-fabricated nanowires 10. The light of the light source may be unpolarized. Large areas of the substrate 20 having the pre-fabricated nanowires 10 may then be etched simultaneously. The light source 30 emits the spectrum for inducing the etching. When etching InP nanowires and aiming for a desired wire diameter of 10 nm the spectrum has a minimum wavelength of 820 nm. The light source further emits a further wavelength between 820 and 254 nm. The light having the further wavelength is able to induce etching of the pre-fabricated semiconducting nanowires 10 having the desired wire diameter d. To largely reduce etching of the nanowires 10 having the desired wire diameter d, the light emitted by the light source 30 is spectrally filtered by a filter 31 for substantially reducing light having the further wavelength prior to inducing the etching. A long-pass filter, a band-pass filter such as an interference filter and/or a monochromator may be used to substantially prevent etching of nanowires having the desired wire diameter. Applying an appropriate filter the nanowires are size-selectively photo-etched down to the desired wire diameter. The etching process typically takes 2-10 hours. Alternatively, a laser may be used as a light source 30. The laser beam of the laser may be linearly polarized thus the light inducing the etch treatment is linearly polarized along an axis. The laser may be a tunable laser such as e.g. a diode laser or a Titanium Sapphire laser.

The light of the light source 30 may be focused on the substrate 20 having the pre-fabricated nanowires 10 by an objective 33. The power density of the light inducing the etching depends on the magnification of the objective used. The magnification may be e.g. between 50 and 1000×. The power density may be between 0.5 and 10 kW/cm$^2$ at a wavelength of 457 nm. The polarization vector may be rotated by, e.g., a polarization rhomb. The maximum excitation polarization ratio obtained with an InP nanowire is 0.95. A blue shift and/or an intensity increase in the photoluminescence is typically observed after photo-etching 3-120 minutes. The maximum increase in emission intensity obtained is a factor 1300.

Prior to subjecting the prefabricated nanowires to the etch solution the nanowire may be subjected to an aqueous solution of 20 vol. % of HF which may remove an oxide at the outer surface of the nanowire. Such a treatment may reduce the process time required for reducing the wire diameter by the light induced etch treatment.

During the etching process the nanowire may emit a light signal due to, e.g. photo luminescence which is indicative for the wire diameter. The emission intensity as well as the emission wavelength may be monitored by a monitor unit 35 which may provide a signal relating to the intensity of the photoluminescence and/or a signal relating to the wavelength of the photo luminescence. The light source 30 may be controlled in dependence of one or both signals provided by the monitor unit 35. For instance, the light source may be blocked when the monitor unit 35 provides a signal indicating that the photo luminescence has a predefined spectral composition. When using the self-termination of the light induced etching process this allows for reducing and preferably avoiding unnecessary light exposure and process time after the nanowires have the desired wire diameter. To this end the monitor unit 35 and the light source 30 may be connected to a system control unit 36 such as a computer. In the embodiment shown in FIG. 2 the light detected by the monitor unit 35 is collected by the objective 33 and separated from the light inducing the etching by a beam splitter 37. The beam splitter 37 may be a dichroic mirror which is reflecting at the wavelength of the photo luminescence and transparent at the wavelength of the light inducing the etching.

In an embodiment the light induced etching is terminated not by the fact that the light is no longer absorbed due to the quantum confinement. Instead, the etching is terminated when the nanowires have a desired wire diameter d at which the light inducing the etching is still absorbed. In order to control the wire diameter d during the etching, the light emitted by the nanowires 10 is monitored, e.g. by the monitor unit 35, and depending on the spectral composition and/or the intensity of the light emitted by the nanowires 10 the application of the light inducing the etching is terminated. To this end the light source 30 may be switched off or may be blocked by a shutter, not shown.

This method is based on the insight that the light emitted by the nanowires 10 during the light induced etching is indicative for the wire diameter d of the set of nanowires being etched. The thinner the nanowires 10 get the more blue shifted is the light emitted by the nanowires. Thus, by monitoring the wavelength of the light emitted by the nanowires 10 during the etching the time at which the light application has to be stopped in order to obtain the desired wire diameter may be determined.

In an embodiment a set of randomly oriented pre-fabricated nanowires 10 is provided. This set may be obtained e.g. one of the following ways: The nanowires 10 may be grown on a substrate 20 having a textured surface, parts of the textured surface having random orientations. This may result in random orientated nanowires 10. Alternatively, the nanowires 10 may be detached from the substrate 20 and may be dispersed in a solvent by ultrasound or by mechanically wiping the nanowires 10 off. The nanowires 10 may be dissolved in a solvent of e.g. any alkane or alkanol $C_2$-$C_{12}$. The nanowires may be etched according to the method of the invention by illuminating a container which comprises the nanowires in a solution. The container and the solvent are at least partly transparent for the light inducing the etching. The container and the solvent may be at least partly transparent for the light signal indicative for the wire diameter. The container may have a wall comprising glass or quartz.

A solution comprising the nanowires 10 may be deposited on a substrate 20 by dropcasting. The nanowires may be at least partly orientated by using flow assembly or electric field alignment.

Figure 3B:
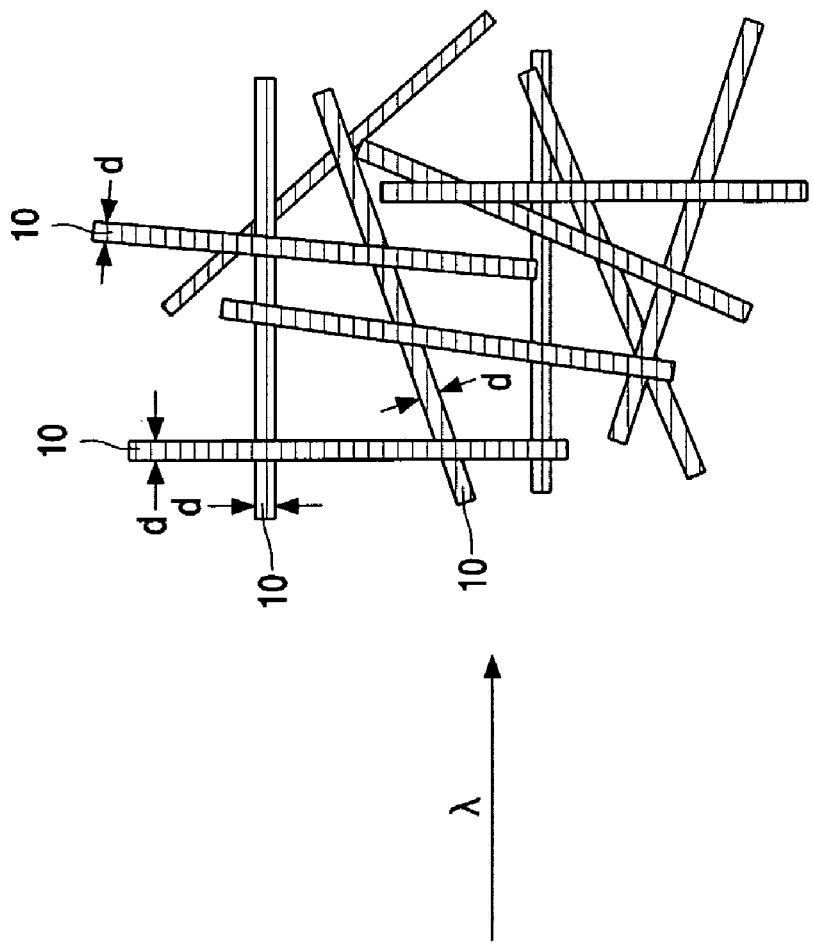
FIGS. 3A and 3B are top views of a set of prefabricated nanowires prior to the etch treatment and after an etch treatment induced by unpolarized light, respectively.
Figure 3A:
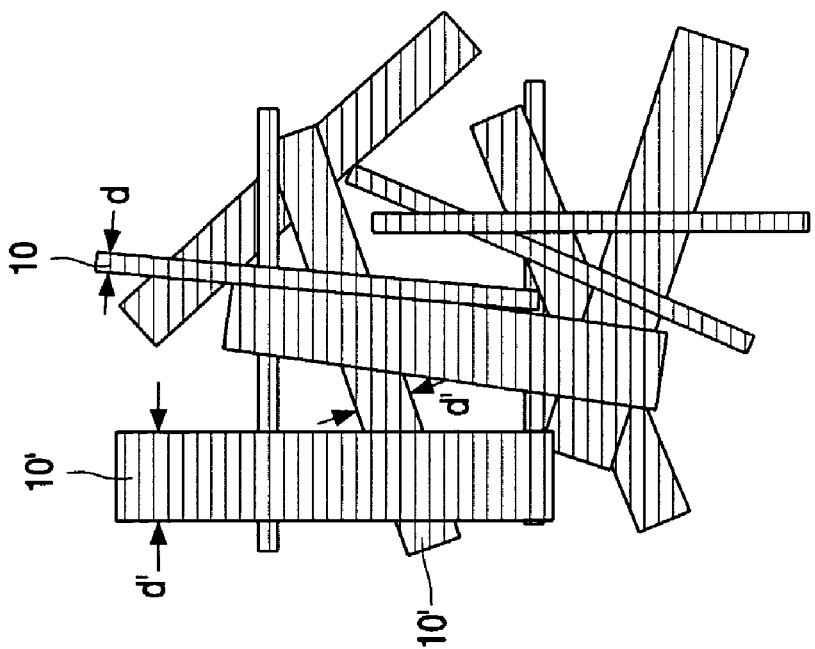

In an embodiment a set of randomly orientated pre-fabricated nanowires 10 shown schematically in FIG. 3A is provided. At least one of the prefabricated nanowires 10' has a wire diameter d' larger than the desired wire diameter d. When providing the set, the set may comprise one or more nanowires 10 having the desired wire diameter d. In an embodiment the set of pre-fabricated nanowires provided prior to the etch treatment shown in FIG. 3A has a relatively broad distribution of wire diameters. Alternatively, the set of pre-fabricated nanowires provided prior to the etch treatment may have a relatively narrow distribution of wire diameters as shown e.g. in FIG. 4A. The set of pre-fabricated nanowires 10 shown in FIG. 3A is treated by a light induced etching using unpolarized light of e.g. a HeXe lamp. The spectrum of the light used for inducing the etching has a minimum wavelength λ which is chosen such that the light induced etching treatment is self terminated at the desired wire diameter d. Alternatively, light having a wavelength shorter than λ may be used and the etch process may be terminated when the light signal indicative for the wire diameter indicates that the set of nanowires has the desired wire diameter. The result of the etching induced by light having the minimum wavelength λ chosen such that the light induced etching treatment is self terminated at the desired wire diameter d is shown schematically in FIG. 3B: After the light induced etch treatment the set of nanowires has a relatively narrow distribution of wire diameters. Substantially all nanowires 10 have the desired wire diameter d, independent of the orientation of the nanowires 10.

The light inducing the etching may be linearly polarized, e.g. along an axis 40 shown schematically between FIGS. 4A and 4B and 4C. In an embodiment the set of pre-fabricated nanowires 10 provided prior to the etch treatment shown in FIG. 4A has a relatively narrow distribution of wire diameters. Alternatively, the set of pre-fabricated nanowires provided prior to the etch treatment may have a relatively broad distribution of wire diameters as shown e.g. in FIG. 3A. The set of pre-fabricated nanowires 10 shown in FIG. 4A is subjected to a light induced etch treatment using linearly polarized light which may be emitted in this polarization state by a light source such as a laser or which may be obtained by using a light source emitting non-linearly polarized light, e.g. unpolarized light, such as a HeXe lamp, and a, in this example linear, polarizer 39. The apparatus 29 may comprise a polarizer 39 shown in FIG. 2, even when the light source 30 does emit polarized light, e.g. because the polarization direction of the light source 30 is different from though not perpendicular to the desired polarization direction and/or because the polarization ratio of the light source 30 is relatively low. The polarizer 39 may be located between the light source 30 and the filter 31, if present, as shown in FIG. 2. Alternatively, the polarizer 39 and the filter 31 may be interchanged which may be advantageous, e.g. when the transmission of the filter 31 depends on the polarization direction. The polarization direction of the light inducing the etching may be rotated to obtain the desired polarization along axis 40 by an optical element 38 shown in FIG. 2 and well known in the art such as a half-lambda plate or a combination of mutually tilted mirrors.

The absorption of the linearly polarized light by the nanowires 10 depends on their orientation: nanowires 10 whose longitudinal axis is parallel to the axis 40 along which the light is polarized, absorb the light relatively effectively whereas nanowires 10 whose longitudinal axis is perpendicular to the axis 40 absorb the light relatively ineffectively. The etching efficiency depends on the absorption of the light. The more photons are absorbed the more effective is the etching. Therefore, the etching induced by linearly polarized light is anisotropic, i.e. nanowires 10 with their longitudinal axis parallel to the axis 40 are etched relatively efficiently whereas nanowires 10 whose longitudinal axis is perpendicular to the axis 40 are etched relatively ineffectively.

After the light induced etch treatment those nanowires 10a whose longitudinal axis is parallel to the axis 40 have the desired wire diameter d, whereas those nanowires 10b whose longitudinal axis is perpendicular to the axis 40 are etched substantially less efficient, i.e. after the etch treatment they have a wire diameter db which is substantially the same as prior to the etch treatment, see FIG. 4B. For nanowires whose longitudinal axis is neither parallel nor perpendicular to the axis 40, exemplary indicated by reference numerals 10c and 10d, the absorption efficiency is between these two extremes. In general the absorption efficiency scales with a trigonometric function of the angle between the longitudinal axis of the nanowire 10 and the axis 40. As a result the wire diameter of these nanowires with the intermediate position is reduced during the etching, cf. the initial wire diameters dc' and dd' versus the wire diameters dc and dd in FIG. 4B. The reduction in the wire diameter depends on the orientation of the longitudinal axis with respect to the axis 40. The light induced etching may be stopped when the nanowires 10a parallel to the axis 40 have the desired wire diameter d. The time instant when to stop the etch treatment may be determined by monitoring a light signal indicative for the wire diameter. When this light signal comprises a component indicative for the desired wire diameter the etch treatment may be stopped.

After the light induced etch treatment the set of nanowires 10 shown schematically in FIG. 4B has a relatively broad distribution of wire diameters whereas prior to the light induced etch treatment the set of nanowires 10 shown schematically in FIG. 4A had a relatively small distribution of wire diameters. The wire diameter of the nanowires 10 depends on the orientation of the nanowires 10.

The spectrum of the linearly polarized light used for inducing the etching may have a minimum wavelength λ which is chosen such that the light induced etching treatment is self terminated at the desired wire diameter d. Alternatively, light having a wavelength shorter than λ may be used and the etch process may be terminated when the light signal indicative for the wire diameter indicates that at least some of the set of nanowires have the desired wire diameter d.

When light inducing the etch treatment has a minimum wavelength λ chosen such that the light induced etching treatment is self terminated at the desired wire diameter d, the light induced etch treatment may be continued when reaching the state schematically depicted in FIG. 4B. Since the nanowires $10a$ parallel to the axis 40 have the desired wire diameter d, they do not absorb the light inducing the etching relatively effectively anymore. As a result they are etched substantially less efficient. Effectively they may be not etched at all. Since the nanowires $10b$ perpendicular to the axis 40 do not absorb the light inducing the etching relatively effectively either, they are etched substantially less efficient as well. Effectively they may be not etched at all. The nanowires $10c$, $10d$ that have an intermediate orientation are etched relatively efficiently until they reach the desired wire diameter d at which the absorption of the light inducing the etching and thus the efficiency of the etching are largely reduced. The set of nanowires thus obtained is depicted schematically in FIG. 4C.

In addition to the linearly polarized light described above and also referred to as the first component, the set of randomly oriented pre-fabricated nanowires may be illuminated by a second component of light inducing an etch treatment. The second component may be linearly polarized along a second axis perpendicular to the first axis, e.g. parallel to the longitudinal axis of nanowire $10b$ shown in FIGS. 4A-4C. This second component may induce relatively effectively etching of nanowires $10b$ which were etched relatively ineffectively with the first component. The first component may have a first spectrum with a first minimum wavelength $\lambda_1$ and the second component may have a second spectrum with a second minimum wavelength 2 different from the first minimum wavelength $\lambda_1$. The first minimum wavelength $\lambda_1$ and the second minimum wavelength $\lambda_2$ may correspond to an energy of, e.g. 1.6 and 2.0 eV, respectively. The nanowires parallel to the second axis having a band gap smaller than, in this example, 2.0 eV absorb the second component and are thus etched until they have a band gap of, in this example, 2.0 eV. In this way nanowires perpendicular to the axis 40 may be etched effectively as well to a desired wire diameter which may be different from the desired wire diameter d determined by the first minimum wavelength $\lambda_1$.

The first component and the second component may be applied simultaneously, sequentially or partly simultaneously and partly sequentially.

When the second minimum wavelength $\lambda_2$ is different from the first minimum wavelength $\lambda_1$, tone may start with nanowires having a wire diameter which exceeds the largest desired wire diameter.

The first component may have a first intensity and the second component may have a second intensity different from the first intensity. Because the efficiency of the etch treatment depends on the amount of light absorbed by the nanowires being etched and because for polarized light this amount depends on the orientation of the nanowire, nanowires may be etched anisotropically, i.e. depending on their orientation. This may be achieved when the second minimum wavelength $\lambda_2$ is different from the first minimum wavelength $\lambda_1$, but also when they are equal.

The method according to the invention may be used to remove one or more nanowires from the set of pre-fabricated nanowires. In this case the desired wire diameter of the respective nanowires comprises zero. To this end light with photons of an energy of approximately 2.4 eV or more may be used for InP. The light inducing etching of nanowires having a desired wire diameter of zero may be linearly polarized.

The set of pre-fabricated nanowires provided prior to the etch treatment shown in FIG. 5A comprises nanowires $10h$ which are substantially horizontal, nanowires $10v$ which are substantially vertical, and nanowires $10i$ which are intermediate, i.e. neither substantially horizontal nor substantially vertical. When such a set is illuminated by light with a relatively short wavelength such that the light is absorbed by the nanowires until they are falling apart, nanowires may be removed from the set.

In the example of FIGS. 5A and 5B the light is linearly polarized along the axis 40, i.e. it is vertically polarized. In this case the nanowires $10v$ substantially parallel to the axis 40 absorb the light relatively effectively and may be removed from the set whereas the nanowires $10h$ substantially perpendicular to the axis 40 absorb the light relatively ineffectively. As a consequence they are not removed from the set. Whether or not nanowires $10i$ which are intermediate, i.e. neither substantially horizontal nor substantially vertical, are removed from the set depends on the time duration of the illumination. When the illumination is terminated directly after removing the last substantially vertical nanowire $10v$, the nanowires $10i$ may remain. When the illumination is continued, they may be removed as well. The longer the illumination is continued in this case, the better defined is the orientation of the remaining nanowires $10h$.

In the example of FIGS. 5A and 5C the light is linearly polarized along the axis 41 which is perpendicular to axis 40, i.e. it is horizontally polarized. In this case the nanowires $10h$ substantially parallel to the axis 41 absorb the light relatively effectively and may be removed from the set whereas the nanowires $10v$ substantially perpendicular to the axis 41 absorb the light relatively ineffectively. As a consequence they are not removed from the set. Whether or not nanowires $10i$ which are intermediate, i.e. neither substantially horizontal nor substantially vertical, are removed from the set depends on the time duration of the illumination. When the illumination is terminated directly after removing the last substantially vertical nanowire $10h$, the nanowires $10i$ may remain. When the illumination is continued, they may be removed as well. The longer the illumination is continued in this case, the better defined is the orientation of the remaining nanowires $10v$.

When the pre-fabricated nanowires 10 are supported by a substrate 20, during the etch treatment the substrate 20 may have a surface 23 constituted by a part $23a$ supporting the pre-fabricated semiconducting nanowires 10 and another part $23b$ being free from the part $23a$, at least the other part $23b$. The substrate 20 may be homogeneous and entirely consist of a material which is etch resistant, such as e.g. Teflon. The substrate 20 may comprise a first layer 24 which is not etch resistant such as an e.g. native oxide layer on a silicon wafer, and a second layer 25 which is etch resistant, the second layer 25, shown in FIG. 6, constituting the other part $23b$ of the surface 23. The second layer 25 may be connected to the first layer 24 by chemical bonds which results in a relatively strong interconnection between these two layers and consequently in a relatively efficient protection of the first layer 24. The second layer 25 may be composed of one or more materials selected from alkyltriethoxysiloxane and alkyltrimethoxysiloxane such as e.g. aminopropyltrietoxysiloxane (APTES). The alkyl may be propyl (C3), butyl (C4), pentyl (C5) up to C12. The amino-group may be replaced by a mercapto- or carboxyl-group.

Figure 6:
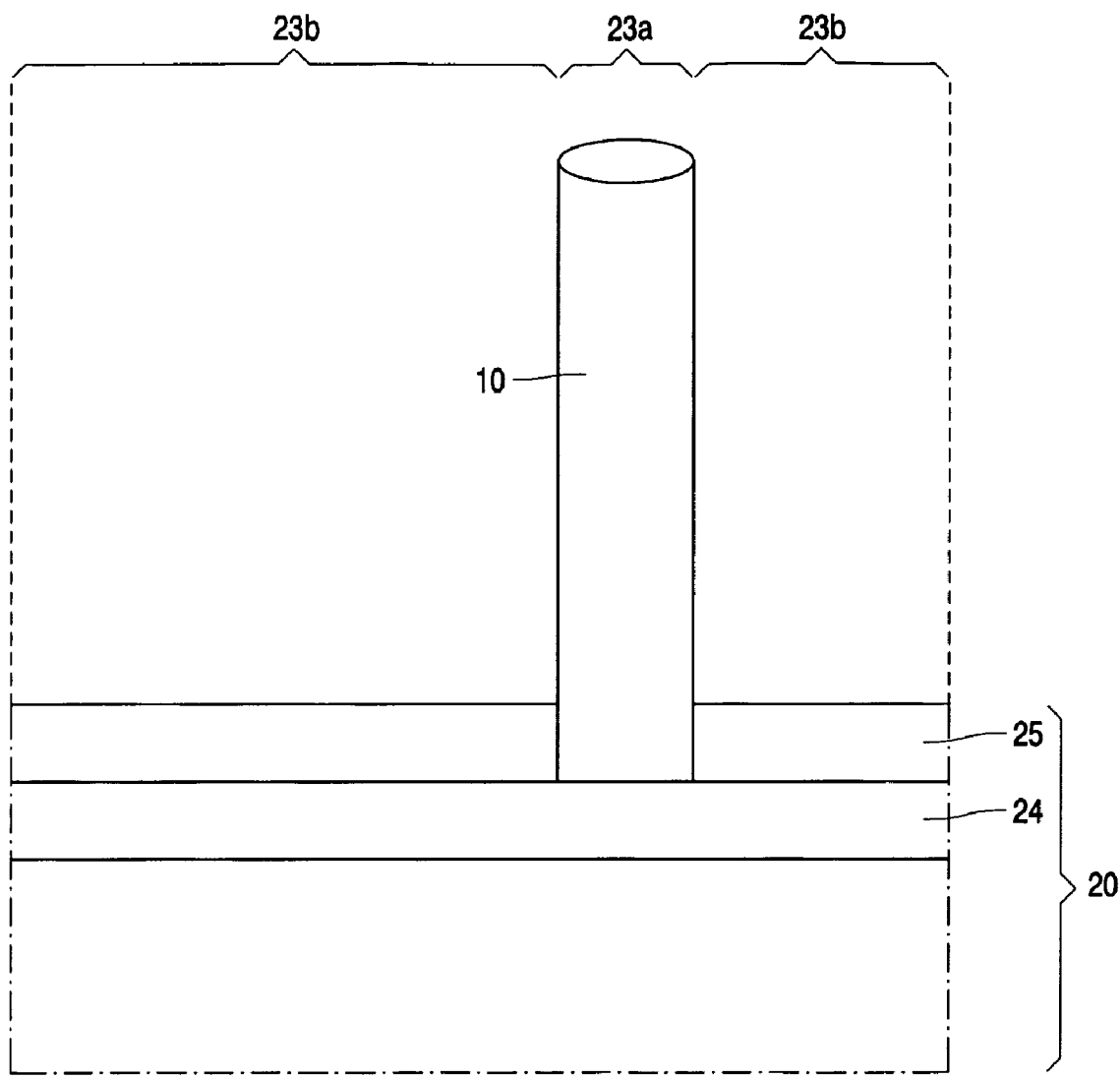
FIG. 6 is a cross section of a substrate with a surface having an etch resistant part.
Figure 7:
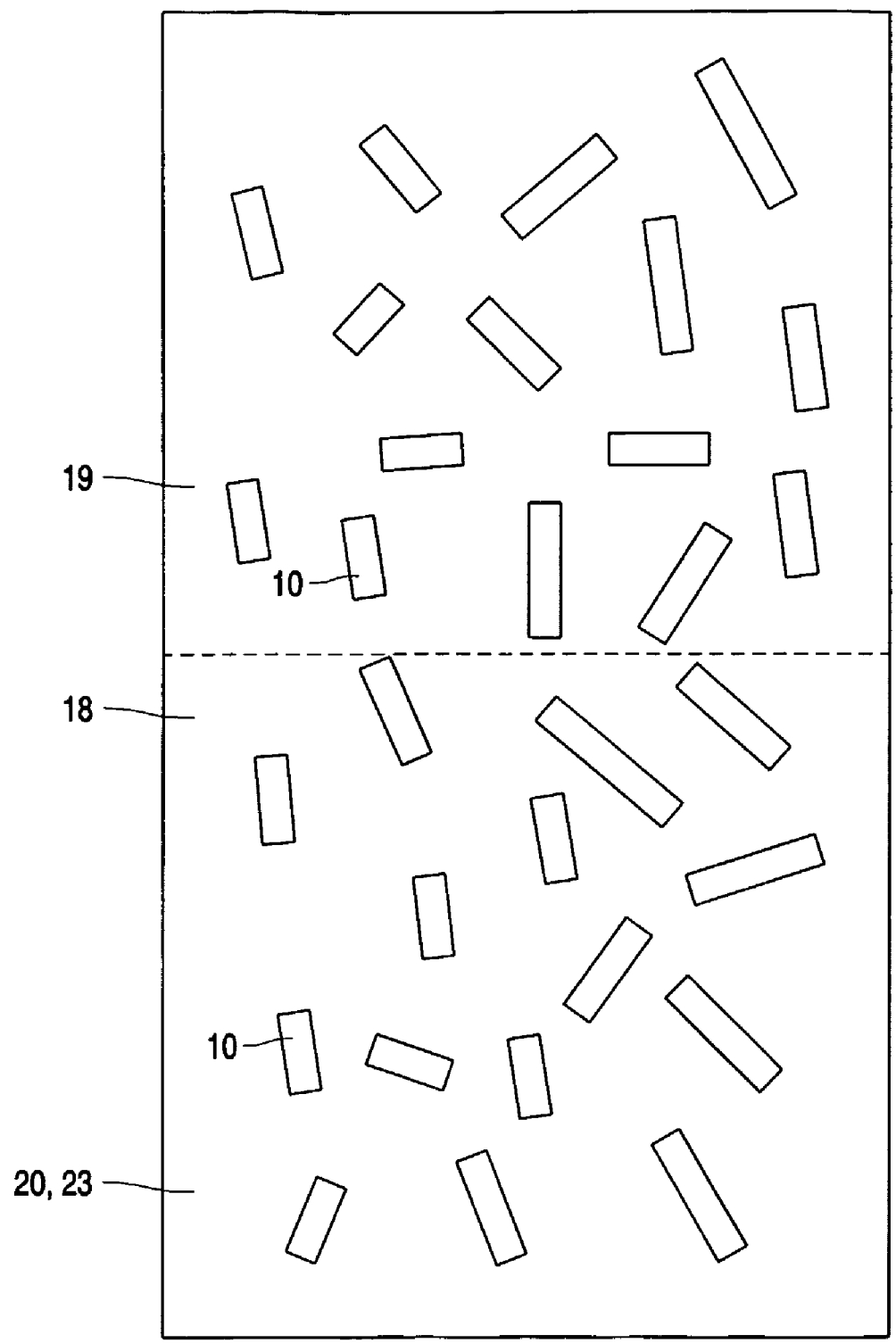
FIG. 7 is a schematic top view of a substrate supporting a set of prefabricated nanowires.
Figures 9A, 9B:
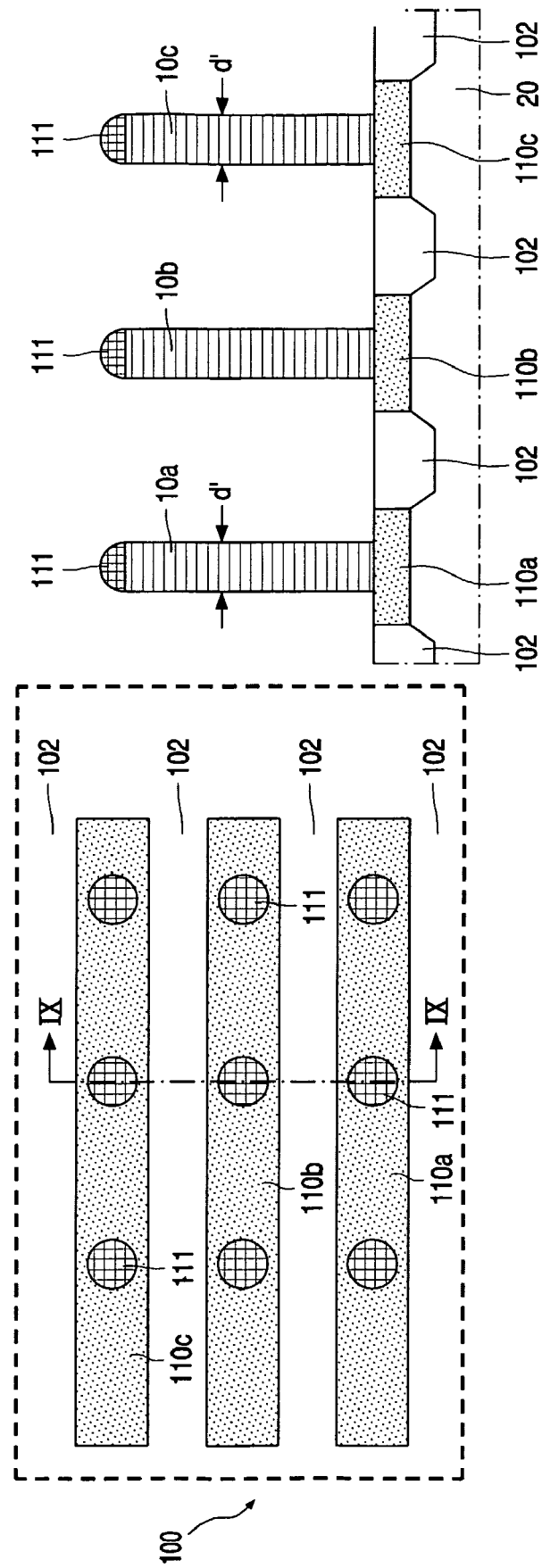
FIGS. 9A and 9B are a schematic top view and a respective schematic cross sectional view along line IX-IX of FIG. 9A of an electric device comprising a set of prefabricated nanowires at a second stage of the manufacturing process.

In one embodiment a substrate 20 having a non-etch resistant surface constituted by layer 24 such as a silicon wafer with an, e.g. native, oxide is provided with a metal film to create nanoparticles which serve as catalyst for the nanowire growth described above. After the growth of the nanowires 10 the surface 23 of the substrate 20 having the nanowires is provided with the second layer 25 which is APTES. The substrate supporting the prefabricated nanowires is immersed in a solution of 0.5% APTES in ethanol for 10 minutes. The second layer 25 selectively binds, i.e. it binds with the oxide constituting the first layer 24 and not with the nanowires 10 which may be composed of InP or any other semiconductor except for silicon. The resulting structure is shown in FIG. 6.

In this embodiment the step of providing the pre-fabricated semiconducting nanowires comprises the sub-steps of providing the substrate 20 which may have a first layer 24. At least a part of the substrate 20 is not etch resistant. The semiconducting nanowires 10 are grown on a surface 23a of the substrate 20. The semiconducting nanowires thus grown are the pre-fabricated semiconducting nanowires 10. After the step of providing the pre-fabricated semiconducting nanowires 10 and prior to the step of reducing the wire diameter of the at least one pre-fabricated nanowire 10 by etching as described e.g. above, the part 23b of surface 23 of the substrate 20 is covered by an etch resistant layer 25.

In another embodiment a substrate 20 is formed by providing a silicon wafer with a native oxide as first layer 24. Then the first layer 24 is proved with the second layer 25 which may be composed of APTES. Subsequently, the pre-fabricated nanowires 10 are provided by drop casting a liquid solution comprising the nanowires 10 as described above.

When the pre-fabricated nanowires 10 are supported by and distributed over a surface 23 of the substrate 20, a first part 18 of the surface may be irradiated by light for inducing the etch treatment whereas a second part 19 of the surface free from the first part 18 is not being irradiated. In this way the nanowires in the second 19 part are not etched whereas those in the first part 18 are etched. As a result the nanowires in the first part 18 of the surface 23 have the desired wire diameter after the etch treatment whereas those in the second part 19 still have their initial wire diameter. The nanowires 10 in the first part 18 may be removed by etching induced by light.

In an embodiment the first part 18 of the surface 23 is irradiated by a first light intensity and the second part 19 is irradiated by a second light intensity smaller than the first light intensity. As a result the nanowires in the first part 18 are etched more efficiently than those in the second part 19. When the light induced etching treatment is stopped, e.g. by blocking the light source 30, before the etching of the nanowires in the second part 19 is self terminated, the nanowires 10 in the first part 18 have acquired a smaller wire diameter than those in the second part 19.

The etching of the nanowires in the first part 18 may be self terminated or it may be stopped prior to reaching the wire diameter at which the etching is self terminated. In the latter case the light source 30 may be blocked in dependence of the light signal indicative for the wire diameter.

The first part 18 and the second part 19, which may not be irradiated or which may be irradiated with the second intensity, may be defined by a mask. The mask may be a separate part of the apparatus 29. The mask may be integrated in filter 31 and/or in plate 22. When part 19 is not irradiated, the mask blocks the light directed to the second part 19. When part 19 is irradiated with the second intensity smaller than the first intensity, the mask partly blocks the light directed to the second part 19. The mask may be etch resistant and may be provided directly to the second part 19 prior to providing the etch solution. Instead of a mask the light may be provided as an, e.g. focused, light spot which is scanned over the surface 23. The scan speed may be modified to change the effective intensity, i.e. areas where the scan speed is relatively low are etched relatively efficiently whereas areas where the scan speed is relatively high are etched relatively inefficiently. Alternatively or in addition, the light may be modulated in intensity and or minimum wavelength during the scanning as function of the position. To this end the apparatus may comprise a scan unit which is controlled by the system control unit.

In an embodiment the first part 18 of the surface 23 may be irradiated by light having a first minimum wavelength, the second part 19 free from the first part 18 of the surface 23 may be irradiated by light having a second minimum wavelength different from the first minimum wavelength. In this way the nanowires in the first part 18 and in the second part 19 may be etched to different desired wire diameters which are determined by the first minimum wavelength and the second minimum wavelength, respectively.

When irradiating the first part 18 and the second part 19 with light having different minimum wavelength, the first part 18 and the second part 19 may be irradiated sequentially. A mask may be used to block the light directed to the first part 18 and the second part 19, when etching the second part 19 and the first part 18, respectively. The mask may be similar to the mask described above used for irradiating the first part 18 while not irradiating the second part 19. Alternatively, a patterned filter 31 may be used which has a first area for transmitting light having the first minimum wavelength and a second area for transmitting light having the second minimum wavelength. The first area and the second area being designed such that they transmit the light to the first part 18 and the second part 19, respectively.

The method of manufacturing a set of nanowires according to the invention may be used in a method of manufacturing an electric device 100. The electric device 100 may comprise a set of nanowires 10 having a desired wire diameter. The electric device 100 may comprise nanowires 10 which are each electrically connected to a first conductor 110 and to a second conductor 120 which may be electrically insulated from the first conductor 110.

The electric device 100 may comprise a set of nanowires 10, the set comprising a first subset of nanowires 10a each having a first wire diameter da and a second subset of nanowires 10b each having a second wire diameter db different from the first wire diameter da. The nanowires 10a of the first subset may be attached to a first part of the substrate 20, which in the example of FIGS. 8A-12B is constituted by the first conductor 110a. The nanowires 10b of the second subset may be attached to a second part of the substrate 20, which in the example of FIGS. 8A-12B is constituted by the first conductor 110b and which is free from the first part.

The nanowires 10a of the first subset may be electrically connected to a conductor, which in the example of FIGS. 8A-12B is constituted by the first conductor 110a. The nanowires 10b of the second subset may be electrically connected to a further conductor, which in the example of FIGS. 8A-12B is constituted by the first conductor 110b and which may be electrically insulated from the further conductor.

The method comprises the steps of fabricating the set of semiconducting nanowires 10 having the desired wire diameter according to an embodiment of the method described above, and electrically contacting the nanowires 10 of the set to a first conductor 110 and to a second conductor 120. Successive steps of the method are depicted in FIGS. 8A-12B.

In a first step a substrate 20, which may be a silicon wafer, is provided with isolation zones 102 which may be shallow trench insulation (STI) regions shown in FIGS. 8A and 8B, and with a first conductor 110 for electrically contacting the nanowires 10 to be formed later on. The first electrical conductor 110 may be formed by doping regions of the substrate outside the STI regions. Alternatively or in addition, a conductor may be deposited for forming the first conductor 110. The substrate 20 may be an insulator such as a quartz substrate. In this case the isolation zones 102 are not required. In the embodiment of FIGS. 8A-12B three parallel, mutually insulated first conductors 110 are provided. However, the invention is not limited to three mutually insulated first conductors 110. Alternatively, the first conductor 110 may be electrically conductively be connected to all nanowires 10 of the set, or it may comprise N mutually insulated electrically conductors where N is an integer larger than one. Here and in the remainder of the application the term "mutually electrically insulated" implies that the conductors are not directly electrically connected. It does not exclude that the conductors are electrically connected indirectly, i.e. via one or more additional elements such as e.g. the nanowires 10 and/or the second conductors 120. The substrate 20 may be transparent to visible light.

Onto the first conductors 110 nanoparticles 111 composed of a metal such as e.g. gold may be provided which may act as catalysts for growing the nanowires 10 as described e.g. above. The nanowires 10 are grown at the position of the respective nanoparticles 111. The wire diameter d' of at least one of the pre-fabricated nanowires 10' thus obtained, shown in FIGS. 9A and 9B, may be larger than the desired wire diameter d. To reduce the wire diameter d' of those nanowires 10' whose wire diameter is larger than the desired wire diameter d, the nanowires are subjected to a light induced etch treatment according to the invention. After growing the nanowires 10' and prior to providing the etching solution, the pre-fabricated electric device 100 may be provided with an etch resistant layer such as e.g. APTES to protect the STI regions if present and/or the substrate.

Figures 10A, 10B:
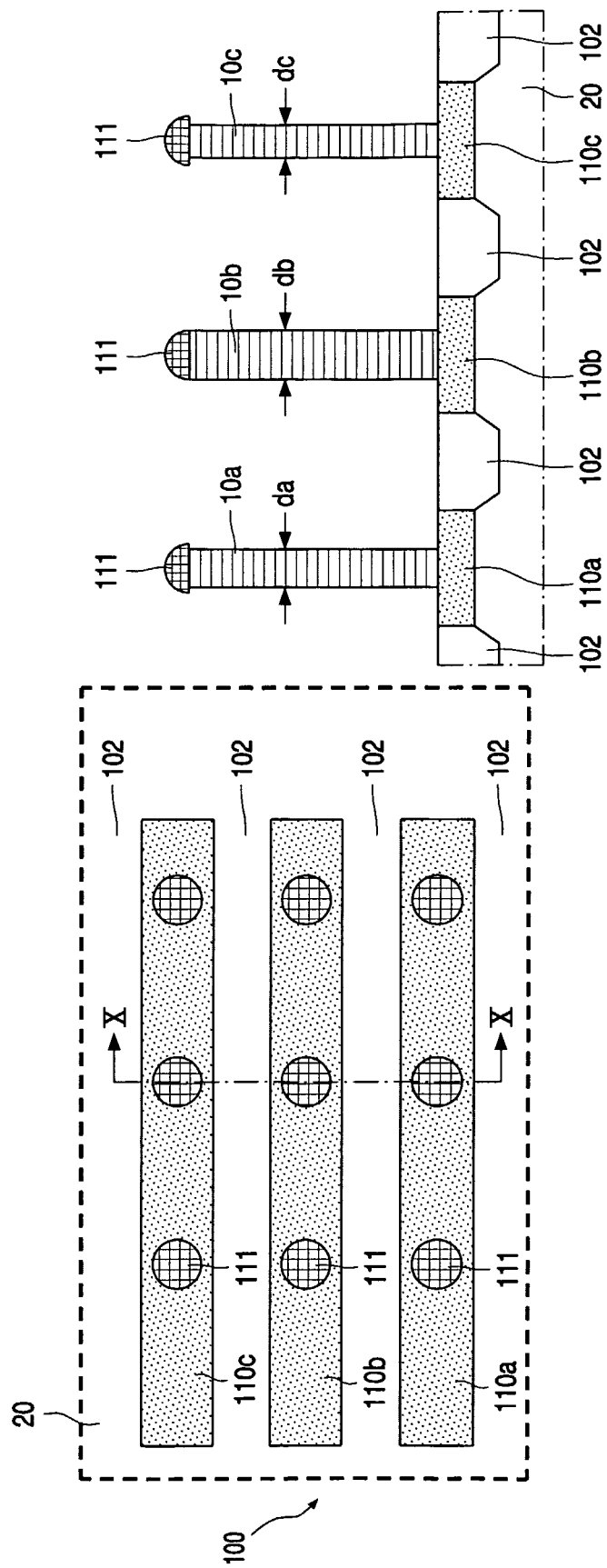
FIGS. 10A and 10B are a schematic top view and a respective schematic cross sectional view along line X-X of FIG. 10A of an electric device comprising a set of prefabricated nanowires at a third stage of the manufacturing process.

For inducing the etch treatment of the nanowires 10a attached to the first conductor 110a shown in FIGS. 10A and 10B light having a first minimum wavelength may be used resulting in a desired wire diameter da. During this etch treatment of the nanowires 10a attached to the first conductor 110a, etching of the nanowires 10b and 10c attached to the first conductor 110b and 110c, respectively, may be prevented, e.g. by using a mask. Subsequently, the nanowires 10c attached to the first conductor 110c shown in FIGS. 10A and 10B may be etched by light induced etching using light having a second minimum wavelength resulting in a desired wire diameter dc. During this etch treatment of the nanowires 10c attached to the first conductor 110c, etching of the nanowires 10a and 10b attached to the first conductor 110a and 110b, respectively, may be prevented, e.g. by using a mask. If required, the nanowires 10b attached to the first conductor 110b may be etched as well to obtain a desired wire diameter db. The etching of the nanowires 10a, 10b, if relevant, and 10c may be self terminating or may be terminated in dependence of a light signal indicative of the wire diameter.

In this method a set of nanowires 10a, 10b, 10c is obtained which consists of a three subsets of nanowires, each subset having a wire diameter which is different from the wire diameter of the nanowires of the other two subsets. Each subset is connected to a particular first conductor 110a, 110b, 110c.

Subsequently, the pre-fabricated electric device 100 shown in FIGS. 10A and 10B may be provided with a, preferably transparent, dielectric layer 130 such as e.g. a spin on glass (SOG), shown in FIGS. 11A and 11B. The upper surface of the pre-fabricated electric device 100 thus obtained may be provided with a second conductor 120 for electrically contacting the upper end portion of the nanowires 10.

The upper end portion of the nanowires 10a, 10b, 10c may be electrically connected to second conductors 120a, 120b, 120c shown in FIGS. 12A and 12B, which are mutually electrically insulated. The first conductors 110a, 110b and 110c and the second conductors 120a, 120b and 120c are mutually perpendicular and form, in this example, a three by three array. In the embodiment of FIGS. 8A-12B one nanoparticle 111 and thus one nanowire 10 is provided at each intersection area defined by the first conductors 110 and the second conductors 120 which define an, in this example rectangular three by three, array. The invention is not limited to an array of this shape or size. The invention is not limited to just one nanoparticle 111 and one nanowire 10 per intersection area. Instead some or all intersection areas may have more than one nanoparticle 111 and one nanowire 10.

The second conductor 120a, 120b, 120c may be at least partly transparent to visible light. They may be composed e.g. of indium tin oxide (ITO). The first conductor 110 and/or the second conductor 120 may be composed of zinc or a zinc alloy.

Figure 13:
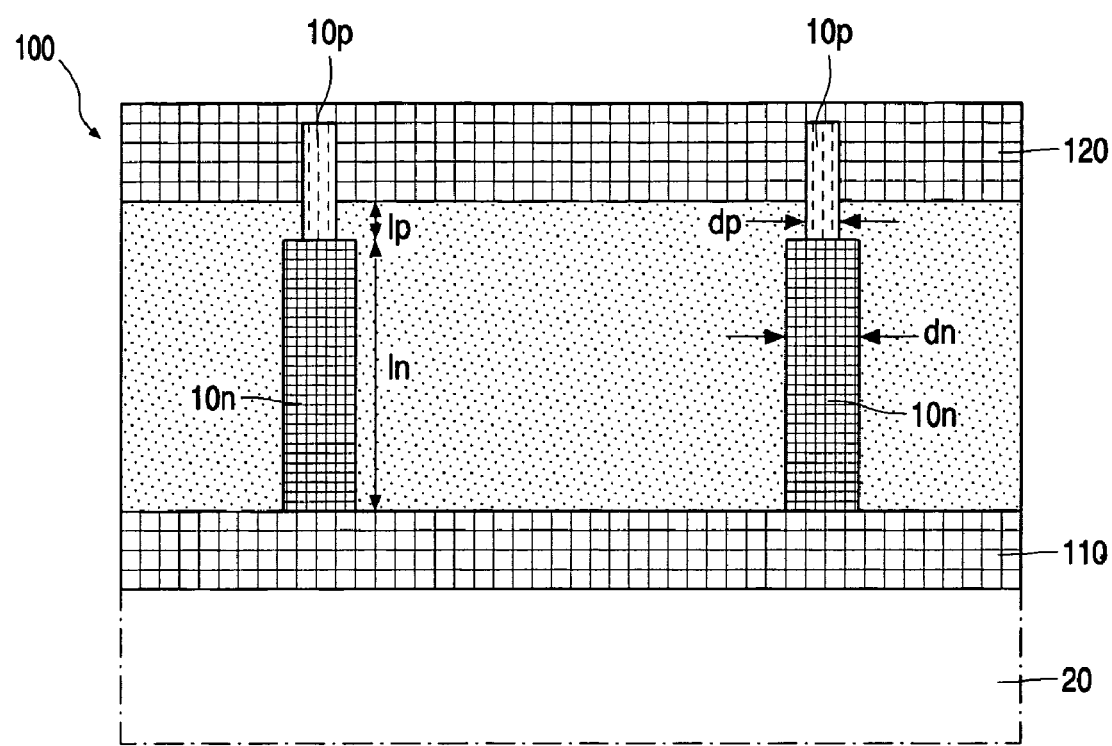
FIG. 13 is a schematic cross section of another electric device.

The nanowires 10a, 10b, 10c may each comprise a p-doped part 10p and a n-doped part 10p forming a p-n-junction, shown in FIG. 13. When sending an electrical current from the first conductor 110 through the nanowire 10 to the second conductor 120, electrons and holes are injected from the respective n-doped part 10 n and p-doped part 10p. When these charge carriers recombine, light is emitted. The light is emitted mainly in the p-doped part 10p close to the p-n junction due to the higher mobility of the electrons as compared to the holes.

In the electric device 100 shown in FIGS. 12A and 12B, the nanowires 10a, 10b and 10c may each comprise a p-n junction. The wavelength of the light emitted by the above described recombination of the holes and electrons depends on the bandgap and hence on the wire diameter at the location of the recombination. In the embodiment of FIGS. 12A and 12B the nanowires 10a, 10b and 10c may have different wire diameters da, db and dc. as a consequence they may emit light of different wavelength. The nanowires may be composed of InP with the n-doped part 10n being doped by e.g. S, Se and/or Te, and the p-doped part 10p being doped by e.g. Zn or Cd. The concentration of the dopants may be e.g. between $10^{17}$-$10^{20}$ cm$^{-3}$.

The p-n junction may serve as a selection device, i.e. a pixel of the array formed by the first conductors 110 and the second conductors 120 may be selected by biasing the respective first conductor 110 and the second conductor 120. The nanowire 10bb located at the intersection of first conductor 110b and the second conductor 120b may be selected by biasing these two conductors. At the intersection more than one nanowire 10bb may be located and selected.

Alternatively, the electrical device 100 may comprise an array of selection devices such as transistors which may be thin film transistors and which may be integrated in the substrate. The selection devices may be addressed by a grid of selection lines for selecting subsets of the nanowires 10.

In the embodiment shown in FIG. 13 the n-doped part 10n is electrically connected to the first conductor 110 having a first distance ln to the p-n junction. The p-doped part 10p is electrically connected to the second conductor 120 having a second distance 1p to the p-n junction which is smaller than the first distance ln. The n-doped part 10n has a wire diameter dn which is larger than a wire diameter dp of the p-doped part 10p.

Due to the presence of the p-n junction the electron-hole pairs generated by the absorption of the light inducing the etching are separated such that the electrons flow to the n-doped part 10n and the holes flow to the p-doped part 10p. The holes are mainly responsible for the light induced etching. The higher hole concentration in the p-doped part 10p results in a more efficient etching and thus in a relatively small wire diameter dp. As a result, the nanowire may have two regions, the n-doped part 10n and the p-doped part 10p, having different diameters dn and dp, respectively. The n-doped region may have a diameter which may be similar to the wire diameter prior to etching. The wire diameter dp of the p-doped part 10p may be predetermined by the minimum wavelength of the light used for inducing the etching. The light signal indicative for the wire diameter may be observed when etching nanowires 10 having a n-doped part 10n and a p-doped part 10p. The light emitted due to recombination of electrons and holes in the p-doped part 10p is indicative for the wire diameter dp of this part. Once the light signal indicates that the desired wire diameter dp is reached, the light inducing the etching may be blocked to prevent any further etching of the n-doped part which may result in an unwanted further reduction of the wire diameter dn of the n-doped part 10n.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of other elements or steps than those listed in a claim. The word "a" or "an" preceding an element does not exclude the presence of a plurality of such elements.

The method of fabricating a set of semiconducting nanowires 10 having a desired wire diameter d comprises the steps of providing a set of pre-fabricated semiconducting nanowires 10', at least one pre-fabricated semiconducting nanowire having a wire diameter d' larger than the desired wire diameter d, and reducing the wire diameter of the at least one pre-fabricated nanowire 10' by etching, the etching being induced by light which is absorbed by the at least one pre-fabricated nanowire 10', a spectrum of the light being chosen such that the absorption of the at least one pre-fabricated nanowire being significantly reduced when the at least one pre-fabricated nanowire reaches the desired wire diameter d.

The electric device 100 may comprise a set of nanowires 10 having the desired wire diameter d. The apparatus 29 may be used to execute the method according to the invention.

The invention claimed is:

1. A method of fabricating a set of semiconducting nanowires having a desired wire diameter, the method comprising the acts of:
   providing a set of pre-fabricated semiconducting nanowires, at least one pre-fabricated semiconducting nanowire having a wire diameter larger than the desired wire diameter;
   reducing the wire diameter of the at least one pre-fabricated nanowire by etching, the etching being induced by electromagnetic radiation which is absorbed by the at least one pre-fabricated nanowire;
   selecting a minimum wavelength of the electromagnetic radiation such that the absorption of the at least one pre-fabricated nanowire is significantly reduced when the at least one pre-fabricated nanowire reaches the desired wire diameter; and
   stopping the electromagnetic radiation when continuing the electromagnetic radiation does not substantially change the desired wire diameter.

2. The method as claimed in claim 1, wherein:
   a radiation source is used which emits the electromagnetic radiation inducing the etching and electromagnetic radiation having a wavelength shorter than the minimum wavelength, and
   the electromagnetic radiation emitted by the radiation source is spectrally filtered for substantially reducing electromagnetic radiation having a wavelength shorter than the minimum wavelength.

3. The method as claimed in claim 1, wherein prior to the reducing act, the wire diameter substantially all the pre-fabricated semiconducting nanowires have a diameter larger than the desired wire diameter.

4. The method as claimed in claim 1, wherein the light inducing the etch treatment is linearly polarized along an axis.

5. The method as claimed in claim 1, wherein the light inducing the etch treatment has a first component being linearly polarized along a first axis and a second component being linearly polarized along a second axis forming an angle larger than zero with the first axis.

6. The method as claimed in claim 5, the first component has a first spectrum with a first minimum wavelength and the second component has a second spectrum with a second minimum wavelength different from the first minimum wavelength.

7. The method as claimed in claim 5, wherein the first component has a first intensity and the second component has a second intensity different from the first intensity.

8. The method as claimed in claim 1, wherein the pre-fabricated semiconducting nanowires are supported by a substrate.

9. The method as claimed in claim 8, wherein the substrate comprises an electrical conductor, the pre-fabricated semiconducting nanowires being electrically conductively connected to the electrical conductor.

10. The method as claimed in claim 8, wherein the substrate has a surface constituted by a first part supporting the pre-fabricated semiconducting nanowires and a second part being free from the first part, at least the second part being etch resistant.

11. The method as claimed in claim 10, wherein the substrate comprises a first layer which is not etch resistant, and a second layer which is etch resistant, the second layer constituting the second part of the surface.

12. The method as claimed in claim 11, wherein the second layer is connected to the first layer by a chemical bond.

13. The method as claimed in claim 11, wherein the second layer is composed of one or more materials selected from alkyltriethoxysiloxane and alkyltrimethoxysiloxane.

14. The method as claimed in claim 8, wherein the providing act comprises the following acts:
   providing the substrate, a surface of the substrate being etchable, and
   growing semiconducting nanowires on the surface of the substrate, the grown semiconducting nanowires being the pre-fabricated semiconducting nanowires, and the substrate having an exposed surface between the pre-fabricated semiconducting nanowires,
   and after the providing act and prior to the reducing act, the exposed surface of the substrate is covered by an etch resistant layer.

15. The method as claimed in claim 8, wherein the pre-fabricated semiconducting nanowires are distributed over a surface of the substrate, a first part of the surface being irradiated by light for inducing the etch treatment, pre-fabricated semiconducting nanowires in a second part of the surface being prevented from etching.

16. The method as claimed in claim 8, wherein the pre-fabricated semiconducting nanowires are distributed over a surface of the substrate, a first part of the surface being irradiated by a first light intensity, a second part of the surface free from the first part of the surface being irradiated by a second light intensity smaller than the first light intensity.

17. The method as claimed in claim 8, wherein the pre-fabricated semiconducting nanowires are distributed over a surface of the substrate, a first part of the surface being irradiated by light having a first minimum wavelength, a second part of the surface being irradiated by light having a second minimum wavelength different from the first minimum wavelength.

18. The method of claim 1, further comprising the acts of:
doping a first part of the at least one pre-fabricated semiconducting nanowire to form a p-doped nanowire; and
doping a second part of the at least one pre-fabricated semiconducting nanowire to form a n-doped nanowire;
wherein the reducing act reduces a diameter of the p-doped nanowire to be smaller than a diameter of the n-doped nanowire so that the p-doped nanowire emits radiation of reduced wavelength as compared to a p-doped nanowire with an unreduced diameter, and the n-doped nanowire provides higher current as compared to an n-doped nanowire with a reduced diameter.

* * * * *